(12) United States Patent
Gordon et al.

(10) Patent No.: US 10,195,465 B2
(45) Date of Patent: Feb. 5, 2019

(54) METHOD AND APPARATUS FOR CONTROLLED PENCIL BEAM THERAPY WITH RAPID BEAM COMPENSATION

(71) Applicant: Pyramid Technical Consultants Inc., Lexington, MA (US)

(72) Inventors: John Stuart Gordon, Henfield (GB); Raymond Paul Boisseau, Waltham, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 0 days.

(21) Appl. No.: 15/840,604

(22) Filed: Dec. 13, 2017

(65) Prior Publication Data
US 2018/0111007 A1 Apr. 26, 2018

Related U.S. Application Data

(63) Continuation-in-part of application No. 15/146,541, filed on May 4, 2016.

(60) Provisional application No. 62/468,216, filed on Mar. 7, 2017, provisional application No. 62/433,417, filed on Dec. 13, 2016.

(51) Int. Cl.
*A61N 5/10* (2006.01)

(52) U.S. Cl.
CPC ......... *A61N 5/1067* (2013.01); *A61N 5/1043* (2013.01); *A61N 5/1045* (2013.01); *A61N 5/1049* (2013.01); *A61N 2005/1034* (2013.01); *A61N 2005/1087* (2013.01)

(58) Field of Classification Search
USPC ....................................... 250/492.3
See application file for complete search history.

(56) References Cited

U.S. PATENT DOCUMENTS

| 4,700,068 | A | * | 10/1987 | McClung, Jr. | ........... | F28F 3/083 |
| | | | | | | 250/251 |
| 5,401,973 | A | * | 3/1995 | McKeown | ........... | H05H 1/0006 |
| | | | | | | 250/396 R |
| 5,854,531 | A | * | 12/1998 | Young | ........... | H05H 7/06 |
| | | | | | | 313/362.1 |
| 7,323,700 | B1 | * | 1/2008 | Ledoux | ........... | H01J 37/1474 |
| | | | | | | 250/396 ML |
| 9,168,392 | B1 | * | 10/2015 | Balakin | ........... | A61N 5/1049 |

* cited by examiner

*Primary Examiner* — Phillip A Johnston
(74) *Attorney, Agent, or Firm* — Intrinsic Law Corp.

(57) ABSTRACT

A control system for fine tuning or spreading a charged particle pencil beam includes a low-inductance, low-power compensation or fine-tuning magnet assembly. The feedback loop that includes the compensation magnet assembly has a faster response rate than the feedback loop that includes the scan nozzle. The compensation or fine-tuning magnet assembly is preferably disposed upstream of the scan nozzle magnet(s) with respect to the beam path to make rapid but minor adjustments to the beam position between iterations of the scan nozzle.

24 Claims, 17 Drawing Sheets

METHOD AND APPARATUS FOR CONTROLLED PENCIL BEAM THERAPY WITH RAPID BEAM COMPENSATION

CROSS-REFERENCE TO RELATED APPLICATIONS

This application is a continuation-in-part of U.S. patent application Ser. No. 15/146,541, titled "Method and Apparatus for Controlled Pencil Beam Therapy," filed on May 4, 2016. This application also claims priority to U.S. Provisional Application No. 62/433,417, titled "Method and Apparatus for Controlled Pencil Beam Therapy with Rapid Beam Compensation," filed on Dec. 13, 2016, and to U.S. Provisional Application No. 62/468,216, titled "Method and Apparatus for Controlled Pencil Beam Therapy with Rapid Beam Compensation," filed on Mar. 7, 2017. Each of the foregoing applications is hereby incorporated by reference.

TECHNICAL FIELD

The present application generally relates to controlling pencil beam treatments and treatment systems for example in the context of proton beam therapy and more particularly to methods for beam tracking and positioning.

BACKGROUND

Charged particle therapy is used to treat certain conditions (e.g., cancer) in patients using focused, collimated or other spatially limited energetic particle beams. The principle generally relies on the controlled and localized deposition of sufficient dose of ionizing radiation in a treatment volume. The treatment volume may be an arbitrary three-dimensional volume (e.g., a cancer tumor) within the patient's body. In some instances, ionizing radiation is used to physically overcome the diseased tissue's survival thresholds and thereby destroy the diseased tissue.

In all such therapy procedures it is important to control the amount and location of the applied therapy beams and fields applied to a patient's body to avoid or minimize harm to healthy tissues and organs in the vicinity of the diseased volume. Surgical planning routines, sometimes employing medical imaging to guide the therapy procedure, are used to define the treatment volume and to prescribe the application of the therapy to the treatment volume. Time-dependent modeling, monitoring and other controls are employed to safely carry out proton therapy and similar treatments because the energy beams used in the treatments can accidentally injure the patients if applied incorrectly.

Pencil beam proton and other light ion therapy is used because of its ability to deliver dose to the patient with greatly improved spatial resolution and accuracy. It employs relatively narrow cross-sectional beams of protons, which can be on the order of a few millimeters in diameter. The advantages of the method require that the proton beam is positioned with a high degree of precision.

FIG. 1 illustrates a basic light ion therapy system such as a pencil beam proton therapy system (PBS) 10. Current proton therapy systems 10 include a proton beam source 100, which can generate a directed beam of ionizing radiation 102 at a desired energy level (typically 30 to 250 MeV). The beam 101 is transported from the source to the scanning system and dose measurement system 120 ("Nozzle"). The beam transport beamline 110 deflects the beam 101 as needed using one or more primary bending electromagnets 112, fine trim electromagnets 114 or other components, as well as scanner deflectors 122 in scan nozzle 120. One or more ion chambers (sometimes "IC") 124 are disposed before the target of the beam. The target is supposed to be at a location in a patient, but it is characterized for control purposes by its projection onto the nominal "isocenter" plane 105. The resulting beam reaching the patient may be deflected, intentionally or unintentionally, scanned or otherwise controlled by factors causing its beam angle and position in three dimensional space to be altered over time. Those practiced in the art have also recognized that the beam tends to deviate from its commanded position between treatment sessions and during treatments according to unwanted variation in magnetic fields and other factors affecting the beam's spatial positioning. These variations are generally imposed onto a series of commanded positions, and can potentially adversely affect the continued accuracy and effectiveness of the treatment by negatively affecting healthy organs in the vicinity of the diseased treatment volume.

If a beam has moved away from its desired trajectory by a clinically unacceptable amount, the beam must be stopped and therapeutic treatment halted. Appropriate adjustments can be made to the system to correct the offset of the beam based on the last measured position error.

Such a process of error correction increases the time for treatment, leading to increased expense. It also requires operator intervention, with an associated possibility of operator error. Extended treatment time may also introduce errors due to patient movement and associated deviations between the actual patient position and diagnostic imaging data. However, error correction may not be possible if the error is too large or if the error cannot be corrected quickly, in which case patient irradiation is abandoned.

Moreover, it is generally not acceptable to retune the beam if such retuning includes the beam reaching the patient as this could compromise the intended dose distribution for the patient in a way that is not correctable.

What is needed is an apparatus and method for maintaining beam alignment without impacting patient treatment. What is also needed is an apparatus and method for improving the performance of the beam scan magnets with respect to their speed and position accuracy.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the disclosure, some of the advantageous features will now be summarized. Other objects, advantages and novel features of the disclosure will be set forth in the following detailed description of the disclosure when considered in conjunction with the drawings, which are intended to illustrate, not limit, the disclosure.

In aspect, the invention is directed to a system for providing real-time correction of a charged particle beam. The system comprises a particle beam generator to generate a generated particle beam parallel to a reference axis; a transport beamline apparatus comprising beamline deflector magnets to generate magnetic fields to deflect said generated particle beam along a defined trajectory towards a scan nozzle; said scan nozzle comprising: at least one scan electromagnet to direct said generated particle beam to a target position on an isocenter plane; a detector apparatus disposed between said at least one scan magnet and said isocenter plane, said detector apparatus configured to output a measured position signal representing a measured position of said deflected particle beam in orthogonal first and second planes, wherein said reference axis is orthogonal to said first and second planes; a compensation electromagnet assembly disposed between said transport beamline apparatus and said scan nozzle, said compensation electromagnet assembly configured to (a) receive from a control system an offset control signal and (b) generate magnetic fields based on said offset control signal to correct a beam offset error; wherein said control system comprises a processor, said control system configured to: receive as an input said measured position signal; determine said beam offset error based on said measured position and a target position of said generated particle beam; and generate said offset control signal based on said beam offset error, and wherein a response rate of a first feedback loop comprising said detector apparatus, said control system, and said compensation electromagnet assembly is faster than a response rate of a second feedback loop comprising said detector apparatus, said control system, and said at least one scan electromagnet.

In one or more embodiments, an inductance of said compensation electromagnet assembly is lower than an inductance of said at least one scan electromagnet. In one or more embodiments, said inductance of said compensation electromagnet assembly is about 150 µH. In one or more embodiments, a maximum magnetic field of said compensation electromagnet assembly is lower than a maximum magnetic field of said at least one scan magnet. In one or more embodiments, said compensation electromagnet is configured to provide a maximum deflection of said generated particle beam of about 3 mm to about 1 cm at said isocenter plane.

In one or more embodiments, said compensation electromagnet assembly includes a combined function electromagnet. In one or more embodiments, said combined function electromagnet includes a multipole electromagnet. In one or more embodiments, said compensation electromagnet assembly includes a first pair of electromagnets to deflect the generated particle beam in said first plane and a second pair of electromagnets to deflect the generated particle beam in said second plane.

In one or more embodiments, said compensation electromagnet assembly is configured to deflect the generated particle beam at an angle to compensate for said beam offset error. In one or more embodiments, said compensation electromagnet assembly is configured to have a maximum magnetic field strength to limit said correction of said beam offset error. In one or more embodiments, said detector apparatus includes a first strip detector configured to measure said first measured position in said first plane and a second strip detector configured to measure said first measured position in said second plane. In one or more embodiments, said first detector apparatus includes a pixelated detector comprising orthogonal detector elements for measuring said first measured position in said first and second planes.

Another aspect of the invention is directed to a system for spreading a charged particle beam. The system comprises a particle beam generator to generate a generated particle beam parallel to a reference axis; a transport beamline apparatus comprising beamline deflector magnets to generate magnetic fields to deflect said generated particle beam along a defined trajectory towards a scan nozzle; a scan nozzle comprising: at least one scan electromagnet to direct said generated particle beam to a target position on an isocenter plane; a detector apparatus disposed between said at least one scan magnet and said isocenter plane, said detector apparatus configured to output a measured position signal representing a measured position of said deflected particle beam in orthogonal first and second planes, wherein said reference axis is orthogonal to said first and second planes; a compensation electromagnet assembly disposed between said transport beamline apparatus and said scan nozzle, said compensation electromagnet assembly configured to (a) receive from a control system a compensation electromagnet control signal and (b) generate magnetic fields based on said compensation electromagnet control signal to spread said measured beam position; wherein said control system comprises a processor, said control system configured to: receive as a first input said measured position signal; receive as a second input a maximum beam spread of said compensation electromagnet assembly; determine a compensation beam spread based on said measured position and said maximum beam spread; and generate said compensation electromagnet control signal based on said compensation beam spread, and wherein a response rate of a feedback loop comprising said detector apparatus, said control system, and said compensation electromagnet assembly is faster than a response rate of a second feedback loop comprising said detector apparatus, said control system, and said at least one scan electromagnet.

In one or more embodiments, said control system is configured to receive as a third input a treatment plan for a subject and a dosage history, the dosage history comprising a beam dosage already delivered to the subject at each position in the isocenter plane. In one or more embodiments, said control system is configured to determine said compensation beam spread based on said third input. In one or more embodiments, said compensation electromagnet control signal includes a compensation beam spread pattern.

In one or more embodiments, an inductance of said compensation electromagnet assembly is lower than inductance of said at least one scan electromagnet. In one or more embodiments, said inductance of said compensation electromagnet assembly is about 150 µH. In one or more embodiments, a maximum magnetic field of said compensation electromagnet assembly is lower than a maximum magnetic field of said at least one scan magnet. In one or more embodiments, said compensation electromagnet is configured to provide a maximum deflection of said generated particle beam of about 3 mm to about 1 cm at said isocenter plane. In one or more embodiments, said compensation electromagnet assembly is configured to deflect the generated particle beam at a plurality of angles to achieve said compensation beam spread.

In one or more embodiments, said compensation electromagnet assembly includes a combined function electromagnet. In one or more embodiments, said combined function electromagnet includes a multipole electromagnet. In one or more embodiments, said compensation electromagnet assembly includes a first pair of electromagnets to deflect the generated particle beam in said first plane and a second pair of electromagnets to deflect the generated particle beam in said second plane.

IN THE DRAWINGS

For a fuller understanding of the nature and advantages of the present disclosure, reference is made to the following detailed description of preferred embodiments and in connection with the accompanying drawings, in which.

Figure 11:
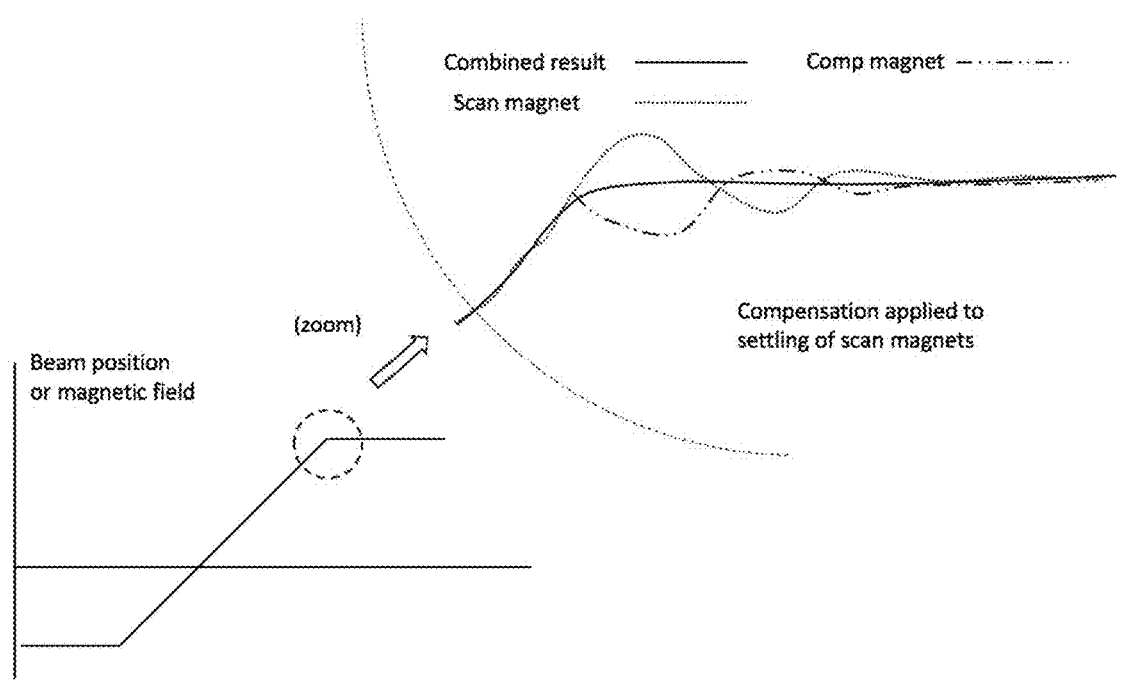
Figure 12:
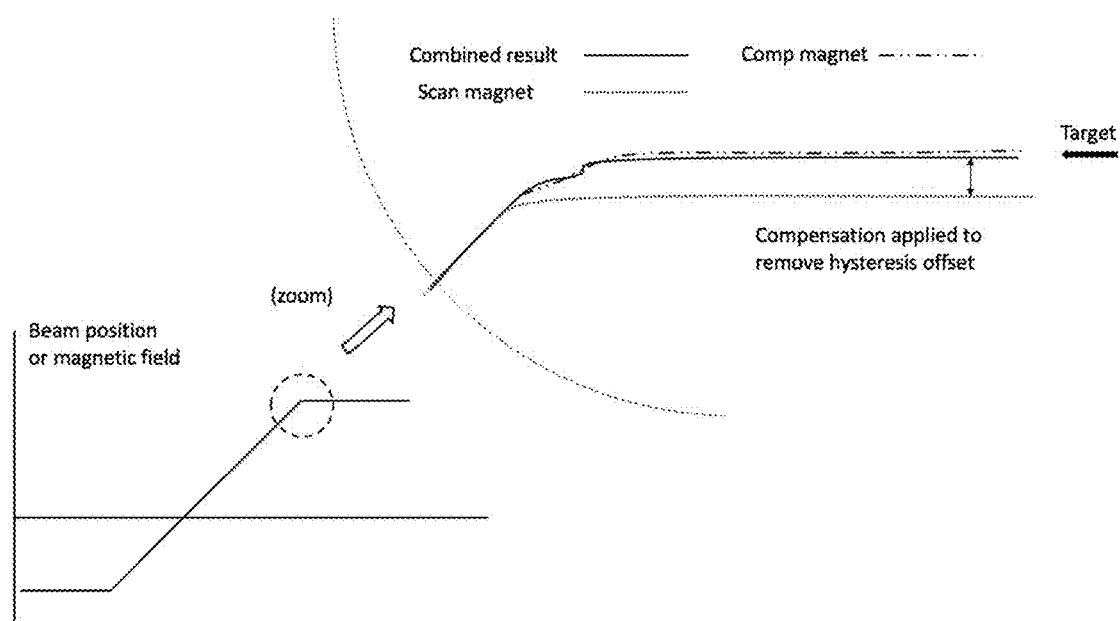
Figure 13:
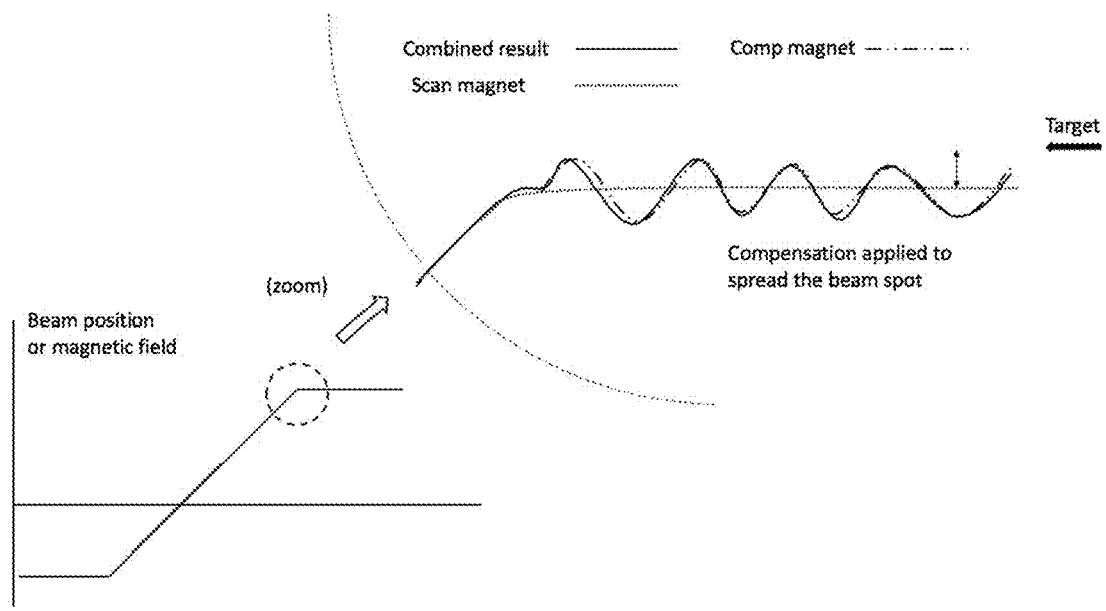
Figure 14:
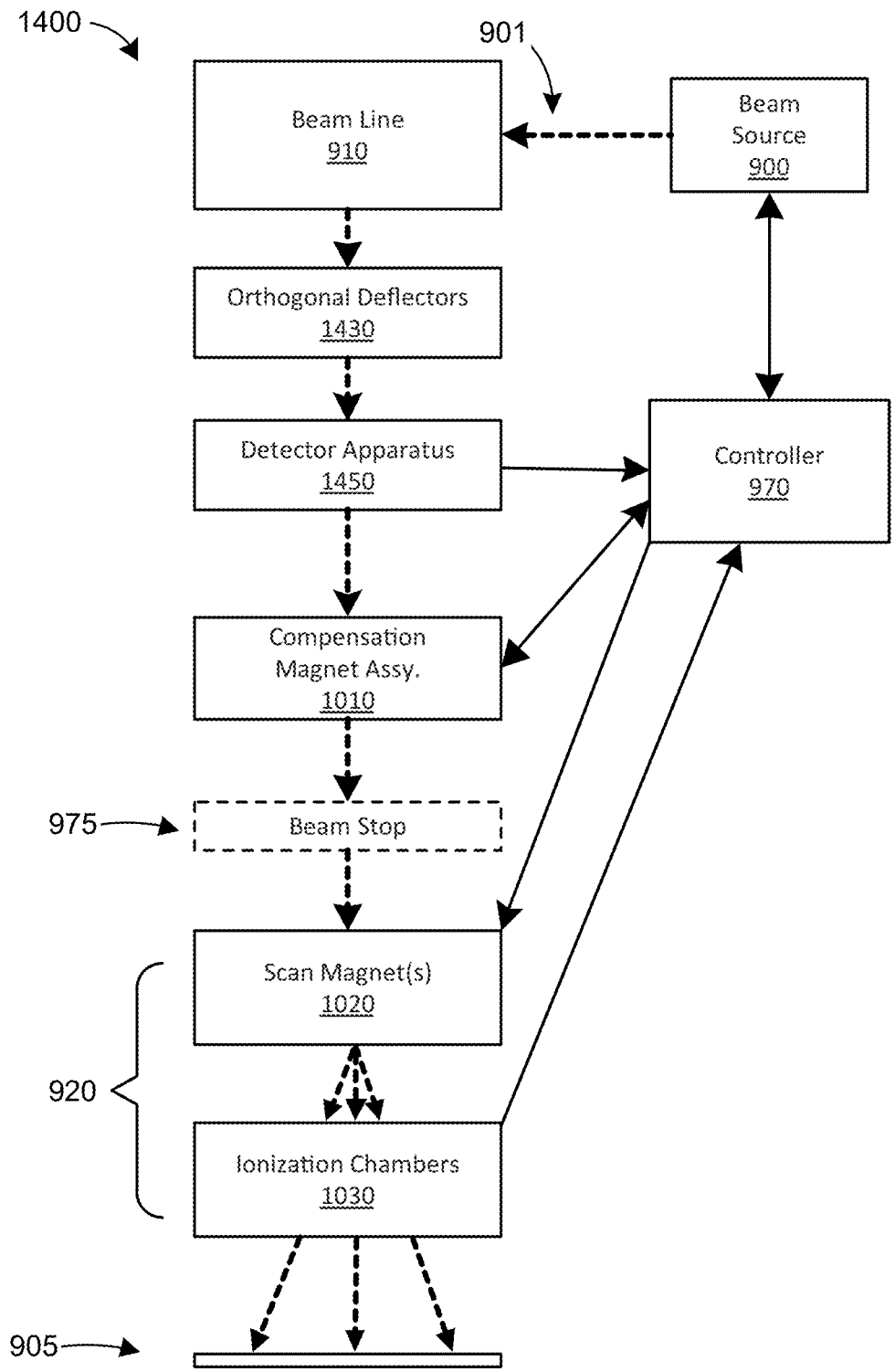
Figure 15:
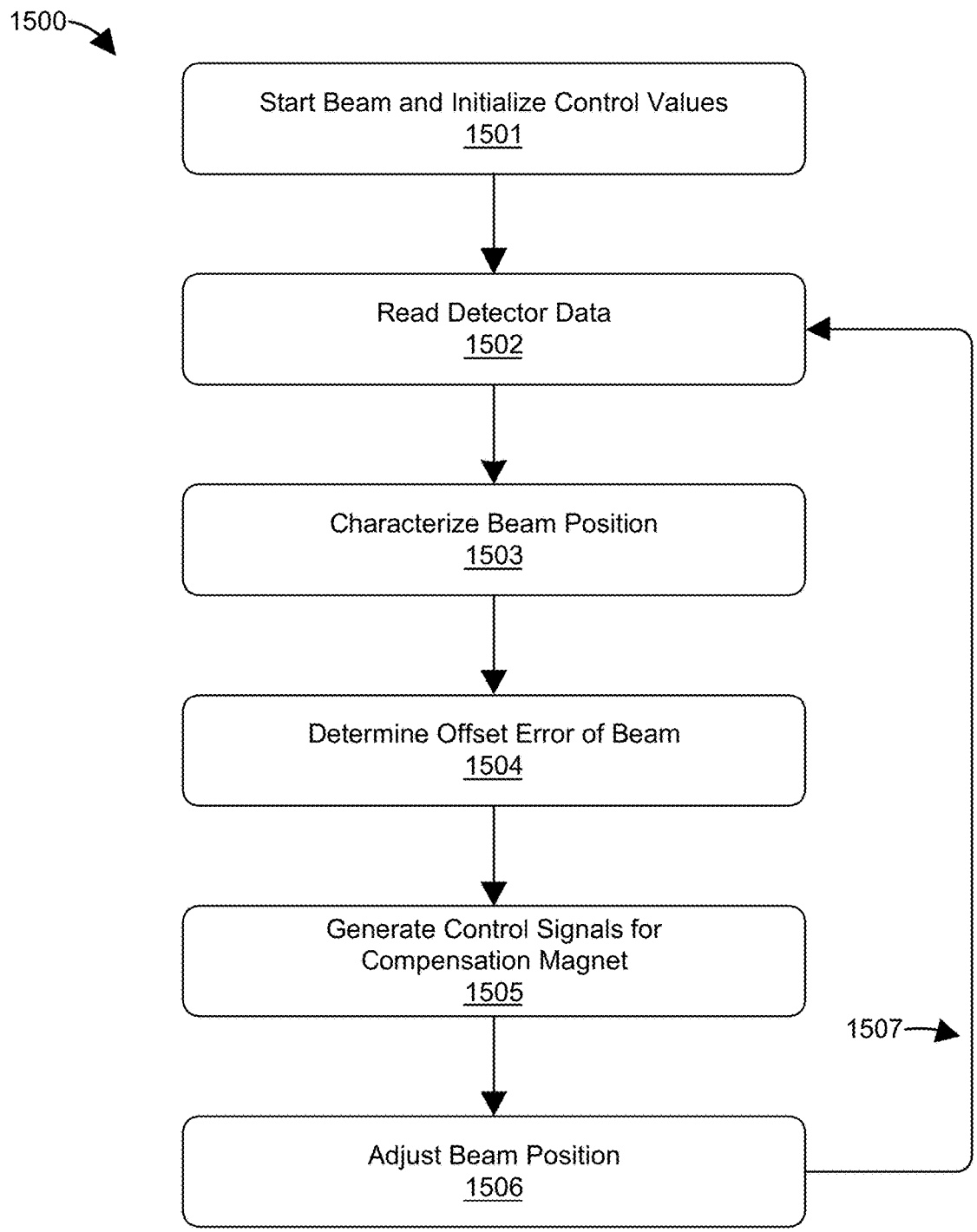
Figure 16:
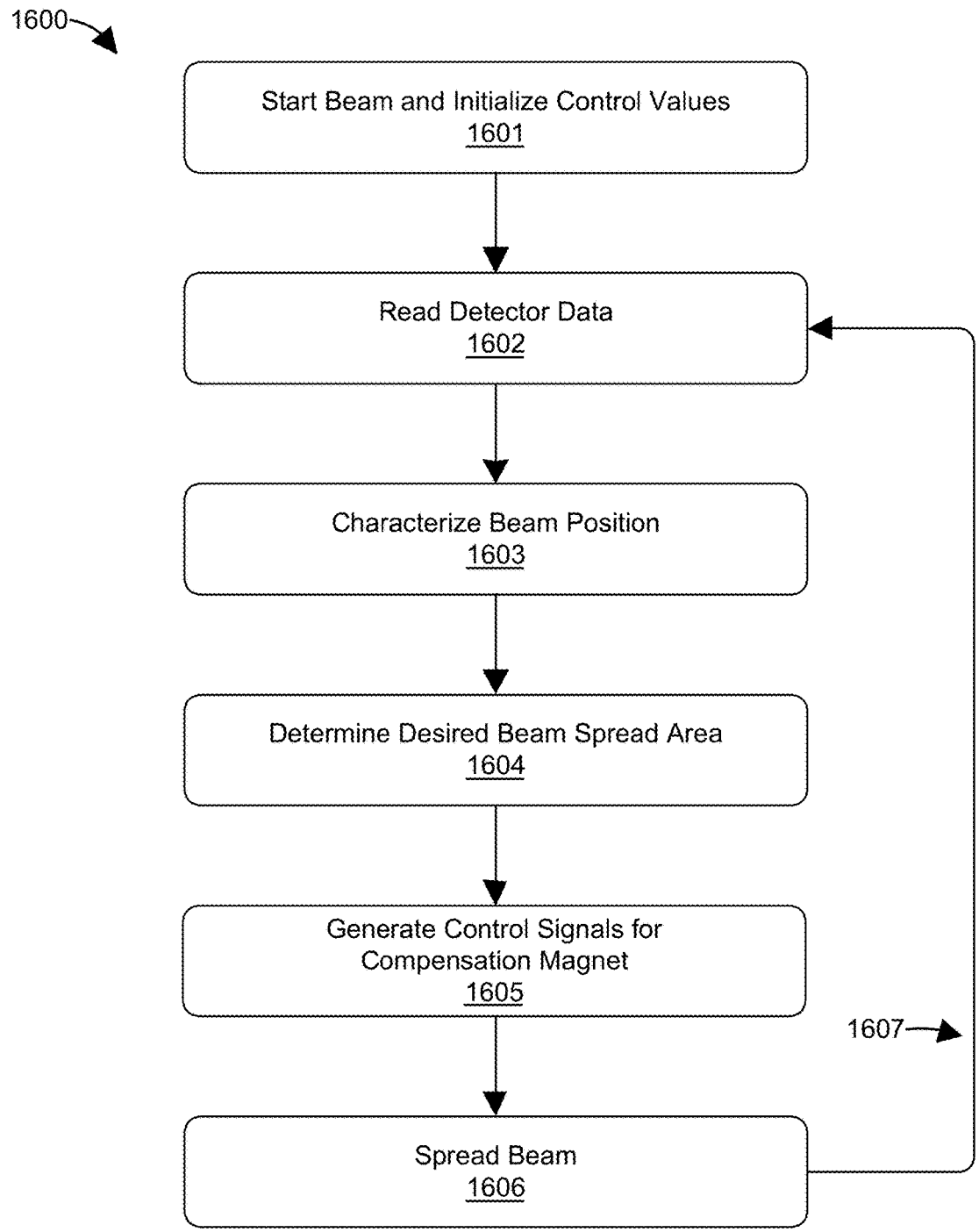
Figure 17:
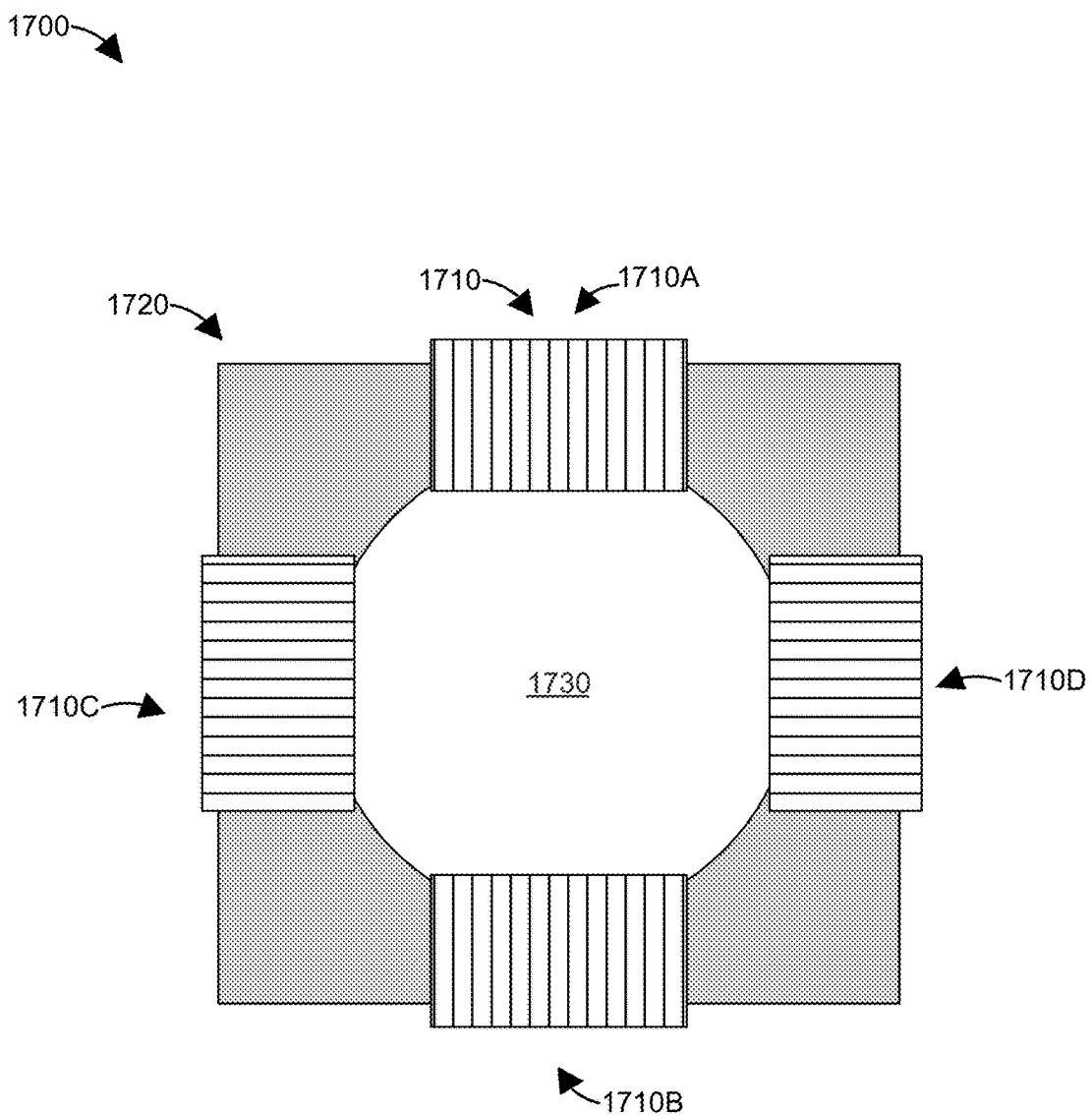

FIGS. 11, 12, and 13 illustrate examples of the fine tuning, adjustment, and beam spread that can be performed by the compensation magnet assembly according to one or more embodiments;

FIG. 14 illustrates a pencil beam system according to one or more embodiments;

FIG. 15 is a flow chart illustrating a method for real-time beam position error correction of a charged particle pencil beam according to one or more embodiments;

FIG. 16 is a flow chart illustrating a method for spreading a position of a charged particle pencil beam according to one or more embodiments; and FIG. 17 illustrates an example of the structure of a compensation electromagnet according to one or more embodiments.

DETAILED DESCRIPTION

Aspects of this disclosure are directed to a novel closed loop control system to adjust the trajectory of a charged particle pencil beam system (PBS). The control system can be used in real time during therapy or during short breaks in therapy without removing the patient from the therapy position. Thus, the control system reduces system downtime needed to align a PBS delivery system during patient treatment. Other aspects of this disclosure are directed to a low-inductance, low-power compensation magnet assembly that can be used to fine tune or spread a charged particle pencil beam in a charged particle pencil beam system.

Aspects of this disclosure recognizes that trajectory correction can require, in general, the ability to control 4 independent parameters. The trajectory control system provides control over the offset of the beam position and the beam angle of the beam in two planes. The offset of the beam position includes a first component with respect to a first plane (e.g., an "x" component with respect to the x-z plane) and a second component with respect to a second plane (e.g., a "y" component with respect to the y-z plane). Similarly, the beam angle includes a first component with respect to a first plane (e.g., an "x" component with respect to the x-z plane) and a second component with respect to a second plane (e.g., a "y" component with respect to the y-z plane).

The "x" and "y" components can be considered independently controlled in many embodiments. For example, these degrees of freedom can be independently controlled in combined function systems having dipole, quadrupole, sextupole, and/or octopole electromagnets which can behave like two independent transport systems (e.g., in the "x" direction and the "y" direction). This task is simplified if done in the last section of the beamline, which is typically a linear arrangement of magnetic (e.g., electromagnetic) elements.

In general, the trajectory control system includes two beam detectors with two-dimensional position capability and either two pairs of orthogonal correctional electromagnets, one pair of combined function correctional electromagnets, or a combination thereof (e.g., one pair of orthogonal correctional electromagnets and one combined function correctional electromagnet). Using the beam detectors, the control system determines the measured offset and measured beam angle of the beam with respect to first and second planes (e.g., x-z and y-z planes). The trajectory control system compares the measured offset and measured beam angle with the model offset and model beam angle to determine an offset error and a beam angle error in each plane. Each pair of orthogonal correctional electromagnets operates to reduce the offset and beam angle errors with respect to a given plane (e.g., x-z or y-z plane). Each pair of correctional magnets deflect the beam by correcting the offset (in the given plane) in the first "leg" and then correcting the beam angle (in the same given plane) in the second "leg." In some embodiments, one, some, or all of the correctional magnets are electromagnets, which allow the respective magnetic fields generated by the electromagnets to be controlled electronically.

Embodiments of the disclosure are directed to a system for providing real-time trajectory correction of a charged particle beam. Error in the trajectory can be resolved into errors in two directions orthogonal to the nominal trajectory of the beam, usually labeled x and y axes, with the z axis being along the nominal trajectory. Measurement and control of the trajectory in these two orthogonal directions can be done independently. The system can include a particle beam generator to generate a particle beam with a trajectory close to close to a nominal axis. The system also includes a transport beamline apparatus comprising a series of electromagnets used to deliver the beam to the scan nozzle, the number and design of these magnets being sufficient to allow the beam to be brought to a trajectory precisely or closely aligned with the nominal entry axis ("reference axis") into the scan nozzle, given the correct magnet settings. The system also includes a scan nozzle comprising a scan magnet system to direct the particle beam to any target position in a patient.

Considering a first error in the beam in an x direction orthogonal to the reference axis, the system also includes a first x axis detector disposed between said transport beam apparatus and said scan nozzle, the first x axis detector configured to output a first signal representing a first measured x position of said deflected particle beam along a first x axis perpendicular to the reference axis. The system also includes a second x axis detector disposed between said first detector and said scan nozzle, the second x axis detector configured to output a second signal representing a second measured x position of the deflected particle beam along a second x axis perpendicular to said reference axis. The offset and angle of the beam trajectory projected onto the x-z plane can be determined from this information. The system also includes a first x correction magnet and second x correction magnet for correction in the x-z plane, the first and second x correction magnets disposed between the particle beam generator and the first detector, the first and second x correction magnets configured to (a) receive an angular deflection control signal and (b) generate magnetic fields to adjust the deflected beam angle in x-z plane.

Considering a second error in the beam in a y direction orthogonal to the reference axis and to the x direction, the system also includes a first y axis detector disposed between the transport beam apparatus and the scan nozzle, the first y axis detector configured to output a first signal representing a first measured y position of the deflected particle beam along a y axis perpendicular to the reference axis. The system also includes a second y axis detector disposed between the first y axis detector and the scan nozzle, the second y axis detector configured to output a second signal representing a second measured y position of the deflected particle beam along a y axis perpendicular to said reference axis. If the path between the first and second detectors is straight, then first and second y axes will be mutually parallel and orthogonal to said x axes. The offset and angle of the beam trajectory projected onto the y-z plane can be determined from this information. The system also includes a pair of second correction magnets for correction in the y-z plane disposed between said particle beam generator and said first y axis detector, the second correction magnets configured to (a) receive an angular deflection control signal and (b) generate magnetic fields to adjust said deflected beam angle in y-z plane.

Detectors for x and y measurements may be conveniently combined into detectors simultaneously sensitive in both axes in order to save space along the beam axis. Thus there would be one first detector sensitive to both x and y position and one second detector sensitive to both x and y position. An example of such a combined detector is a pixelated detector.

Correction magnets in x and y directions may be conveniently combined in "combined function" electromagnets that can deflect simultaneously in orthogonal axes in order to save space along the beam axis. Thus there would be one first combined function correction electromagnet capable of deflecting in both x and y directions and one second combined function correction electromagnet capable of deflecting in both x and y directions. An example of a combined function magnet is a multipole electromagnet such as a quadrupole electromagnet. Quadrupole electromagnets are typically used in the beamline for focus control, but they can also have a dipole field component added so that they can steer or deflect in the x and/or y directions. Thus, an existing quadrupole magnet can be used for focus control and for beam deflecting in the x and/or y directions, which can further save space along the beam axis.

Although the most general correction uses two detector points and four control points to generate a full trajectory correction, a simplified system may use only a single detector point and two control points (e.g., correction electromagnets or a combined function electromagnet) to correct only an offset correction in x and y.

Although the x and y scan magnets are considered part of the scan nozzle, one implementation utilizes the scan magnets as two of the control points.

The system also includes a control system comprising a processor. The control system is configured to receive as inputs said first and second signals for each of x and y axis. The control system calculates for each of x and y axis a measured trajectory of said deflected particle beam based on said first and second measured positions, said measured trajectories including a measured beam angle and a measured offset. The control system also determines a measured beam angle error based on said measured beam angle and a model beam angle of said generated particle beam; determines a measured offset error based on (a) at least one of said measured offset, said first measured position, or said second measured position and (b) a model position of said generated particle beam; generates said beam angle control signal based on said measured beam angle error; and generates said offset control signal based on said measured offset error.

One or more embodiments or implementations are hereinafter described in conjunction with the drawings, where like reference numerals are used to refer to like elements throughout, and where the various features are not necessarily drawn to scale.

Figure 1:
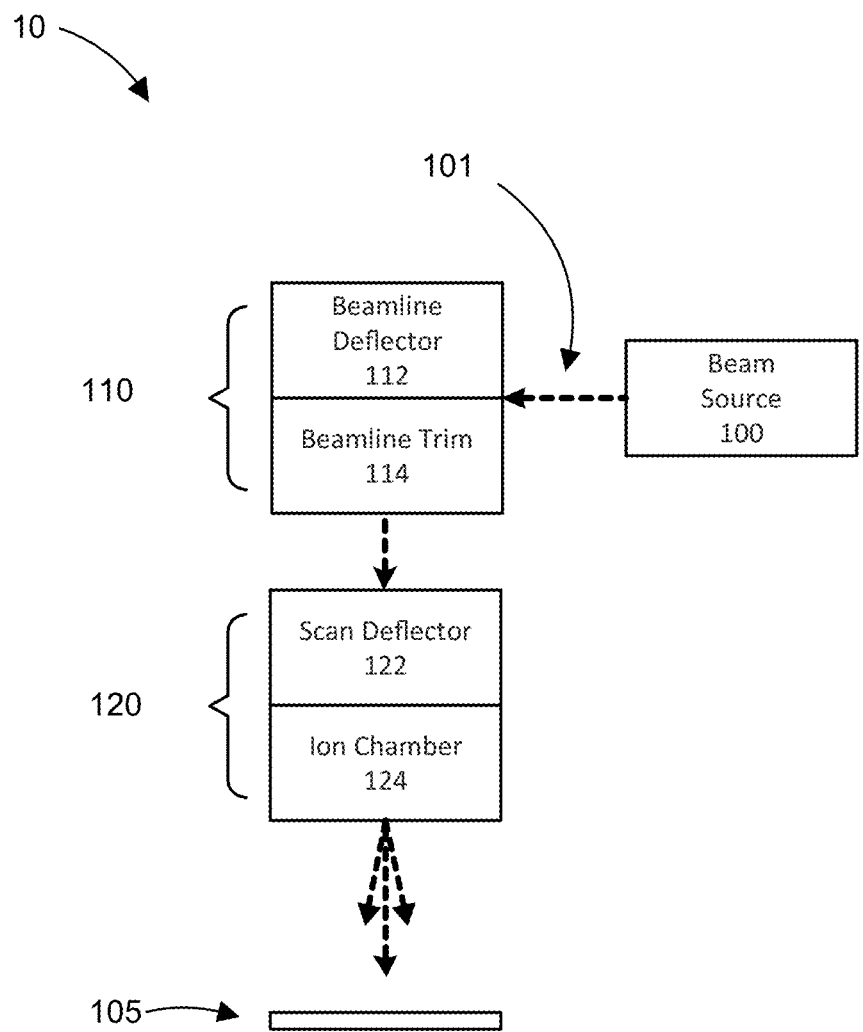
FIG. 1 illustrates a basic proton therapy system according to the prior art.
Figure 2:
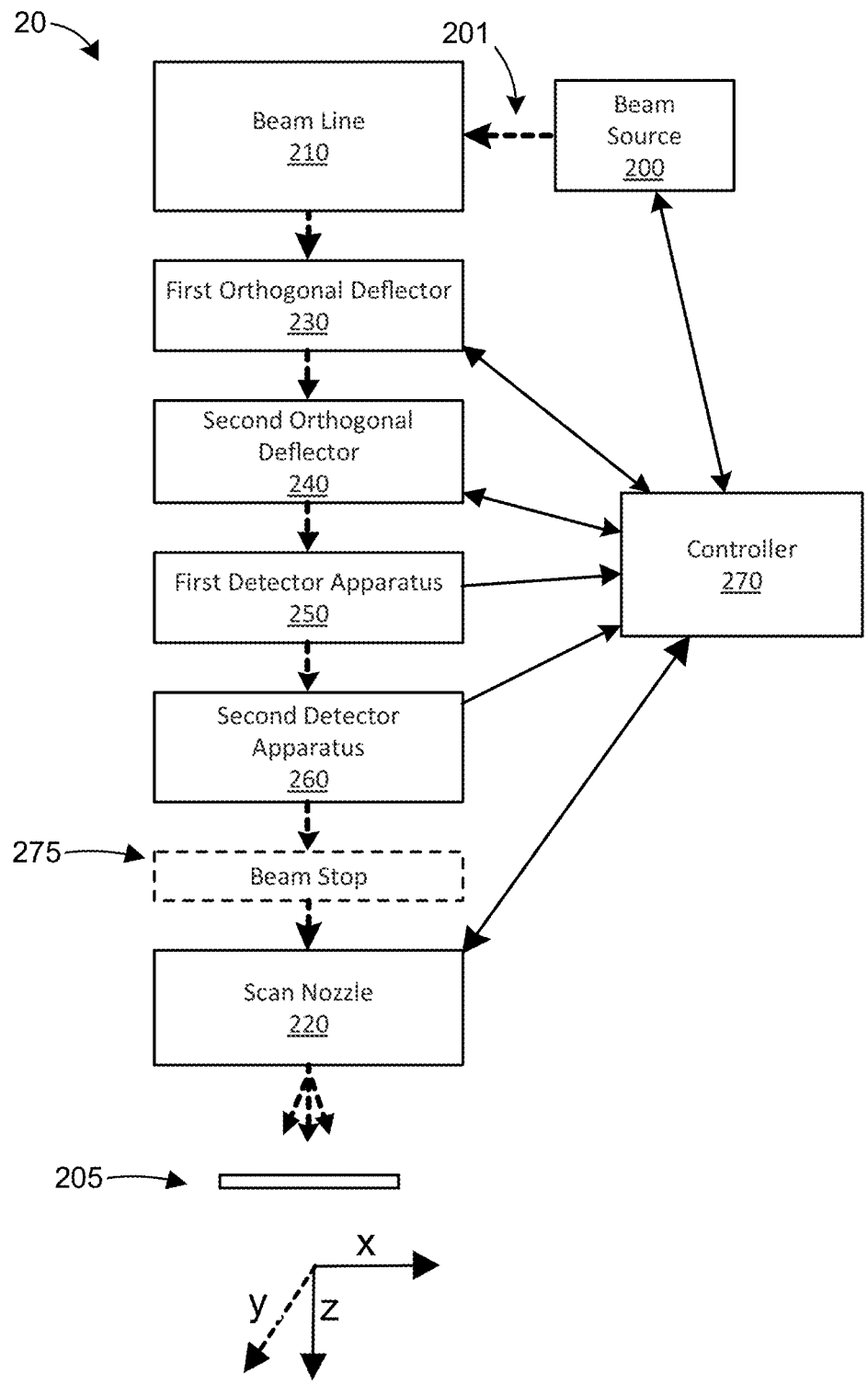
FIG. 2 illustrates a pencil beam system according to one or more embodiments.

FIG. 2 illustrates a PBS system 20 according to an embodiment. The system 20 includes beam source 200, beamline 210, scan nozzle 220, first orthogonal deflector apparatus 230, second orthogonal deflector apparatus 240, first detector apparatus 250, second detector apparatus 260, and controller 270. Beam source 200, beamline 210, and scan nozzle 220 can be the same as respective beam source 100, beamline 110, and scan nozzle 120 described above. First detector apparatus 250 includes one or more IC detectors to measure the two-dimensional position of beam 201 at a first location. For example, first detector apparatus 250 can include a first strip detector for measuring the position of charged particle pencil beam 201 along a first axis (e.g., the "x" axis) orthogonal to the direction of travel (e.g., the "z" axis") of beam 201 and a second strip detector for measuring the position of beam 201 along a second axis (e.g., the "y" axis) orthogonal to the direction of travel of beam 201. Such strip detectors include a plurality of parallel rows of electrodes that can detect the position of the beam in direction orthogonal to the rows. For example, a strip detector having vertical rows of electrodes (e.g., along the "y" axis") can detect the position of the beam in the horizontal direction (e.g., along the "x" axis). In some embodiments, the "x" axis corresponds to the bending direction of local dipole magnets. The "y" axis can be orthogonal to the "x" axis.

Such strip detectors are preferably thin to minimize scatter, energy degradation, and/or distortion of beam 201. An example of such a strip detector can be found in U.S. patent application Ser. No. 14/215,311, entitled "Method and Apparatus for Monitoring a Charged Particle Beam," which is hereby incorporated by reference. Alternatively, first detector apparatus 250 can include a thin pixelated detector that includes a grid of detector elements to measure the position of beam 201 in a given plane (e.g., in the x-y plane, which is orthogonal to the z axis). An example of such a pixelated detector can be found in U.S. patent application Ser. No. 14/493,098, entitled "Method and System for Measuring, Verifying, and Displaying Progress of Dose Delivery in Scanned Beam Particle Therapy," which is hereby incorporated by reference. The '311 and the '098 applications are assigned to the same assignee as this application.

Second detector apparatus 260 can be the same or different than first detector apparatus 250. For example, each detector apparatus 250, 260 can include a pixelated detector or a pair of strip detectors. Similarly, detector apparatus 250 can include a pixelated detector and detector apparatus 260 can include a pair of strip detectors (or vice versa).

Each detector apparatus 250, 260 outputs a signal that represents the two-dimensional position of beam 201. The signal is transmitted through high-speed readout electronics at a data rate that allows the controller 270 to react in a time comparable to the system response time (e.g., about 1 millisecond) to minimize any error in patient dosage. The controller 270 then determines the position (i.e., centroid) of the beam based on the data (e.g., intensity distribution) provided in the signal. When a detector apparatus 250/260 includes a pair of strip detectors, the controller 270 calculates the position (x, y) measured by each strip detector. Thus, the controller 270 calculates an "x" position and a "y" position of beam 201 at the location of each detector apparatus 250, 260.

Using the position of beam 201 at each detector apparatus 250, 260, and the distance between corresponding detectors, the controller 270 calculates the beam angle of beam 201. The beam angle includes an "x" component and a "y" component, which correspond to beam angles Θ and Φ, respectively, measured with respect to the direction of travel of beam 201 as it leaves beam line 210, which is parallel to the z axis. The controller 270 compares the measured beam angles Θ (measured) and Φ (measured) with model beam angles Θ (model) and Φ (model) to determine beam angle errors ΔΘ and ΔΦ.

If strip detectors are used as detector apparatus 250, 260, the beam angle is determined using the distance between the corresponding strip detectors that measure the position of the beam along the same axis (e.g., the strip detector at each location that measures the position along the "x" axis). Similarly, if the first detector apparatus 250 includes a pixelated detector and the second detector apparatus 260 includes a pair of strip detectors, the relevant distance is the distance between the pixelated detector and the strip detector that measured the given component (e.g., "y" position) of beam 201 to determine the "y" component of the beam angle.

In general, the measured beam angles Θ (measured) and Φ (measured) are determined as follows:

$$\Theta = \tan^{-1}\frac{x2-x1}{d\_x} \text{ and } \Phi = \tan^{-1}\frac{y2-y1}{d\_y}$$

where d_x and d_y are the respective distances between the relevant first and second detector apparatus 250, 260. For example, d_x is the distance between the detectors (strip and/or pixelated detectors) that measured the "x" position of beam 201.

In addition, controller 270 determines an offset error in the measured position of beam 201. The offset error can be determined by comparing the measured position of beam 201 with a model position of beam 201. Since the position of the beam 201 includes an "x" component and a "y" component, the offset errors are Δx and Δy. The measured and model positions can be with respect to either detector apparatus 250, 260.

The values of ΔΘ, ΔΦ, Δx, and Δy are used by the controller to calculate new values of the four control signals based on direct calculation, an iterative control algorithm, such as a PI, PID, or other control algorithm as known in the art. The control signals are sent to first and second orthogonal deflector apparatus 230, 240 as discussed below. In some embodiments, the errors are corrected iteratively. As further described below, the first and second orthogonal deflector apparatus 230, 240 can each include a pair of magnets (e.g., electromagnets) to reduce the offset and beam angle errors in a given plane. For example, orthogonal deflector apparatus 230 can include a pair of magnets to reduce the "x" component of the offset Δx and beam angle ΔΘ errors. In another example, orthogonal deflector apparatus 240 can include a pair of magnets to reduce the "y" component of the offset Δy and beam angle ΔΦerrors.

In some embodiments, first and/or second orthogonal deflector apparatus 230, 240 can be disposed between beam source 200 and beam line 210.

Since the detectors in detector apparatus 250, 260 have minimal beam scatter and degradation, the system 20 can be used when a patient is at isocenter 205, for example during therapeutic treatment. Thus, the system 20 provides a closed loop, real time or substantially real time correction/calibration of charged particle pencil beam 201, which greatly reduces system downtime and greatly improves patient throughput.

In some embodiments, an optional beam stop 275 is disposed between second detector apparatus 260 and scan nozzle 220. The beam stop 275 can be configured to block beam 201 during any correction that might require an extended period of time to execute. The beam stop 275 can block the beam 201 from reaching the patient during retuning/calibration/setup, without having to move the patient, and allow beam 201 to pass (and reach the patient) when the retuning/calibration/setup is complete, for example to provide therapy to a patient. For example, beam stop 275 can be used when the energy of beam 201 is adjusted, which is particularly likely to introduce a beam angle error in some systems.

Beam stop 275 can be in a variety of forms, such as a cylinder or sphere with an aperture for allowing beam 201 to pass through in one orientation (e.g., when the aperture is in alignment with beam 201) and block beam 201 in other orientations (e.g., when the aperture is not in alignment with beam 201), for example by rotating the cylinder/sphere. Alternatively, beam stop 275 can be moved into and out of the path of beam 201. For example, beam stop 275 can be a solid object that moves orthogonally to the beam 201 in the "x" or "y" direction, like a swing or guillotine.

In some embodiments, beam stop 275 blocks beam 201 with a sufficiently short actuator time (100 msec or so) to allow for rapid sampling and adjustment of the beam's calibration settings during patient treatment.

Figure 3:
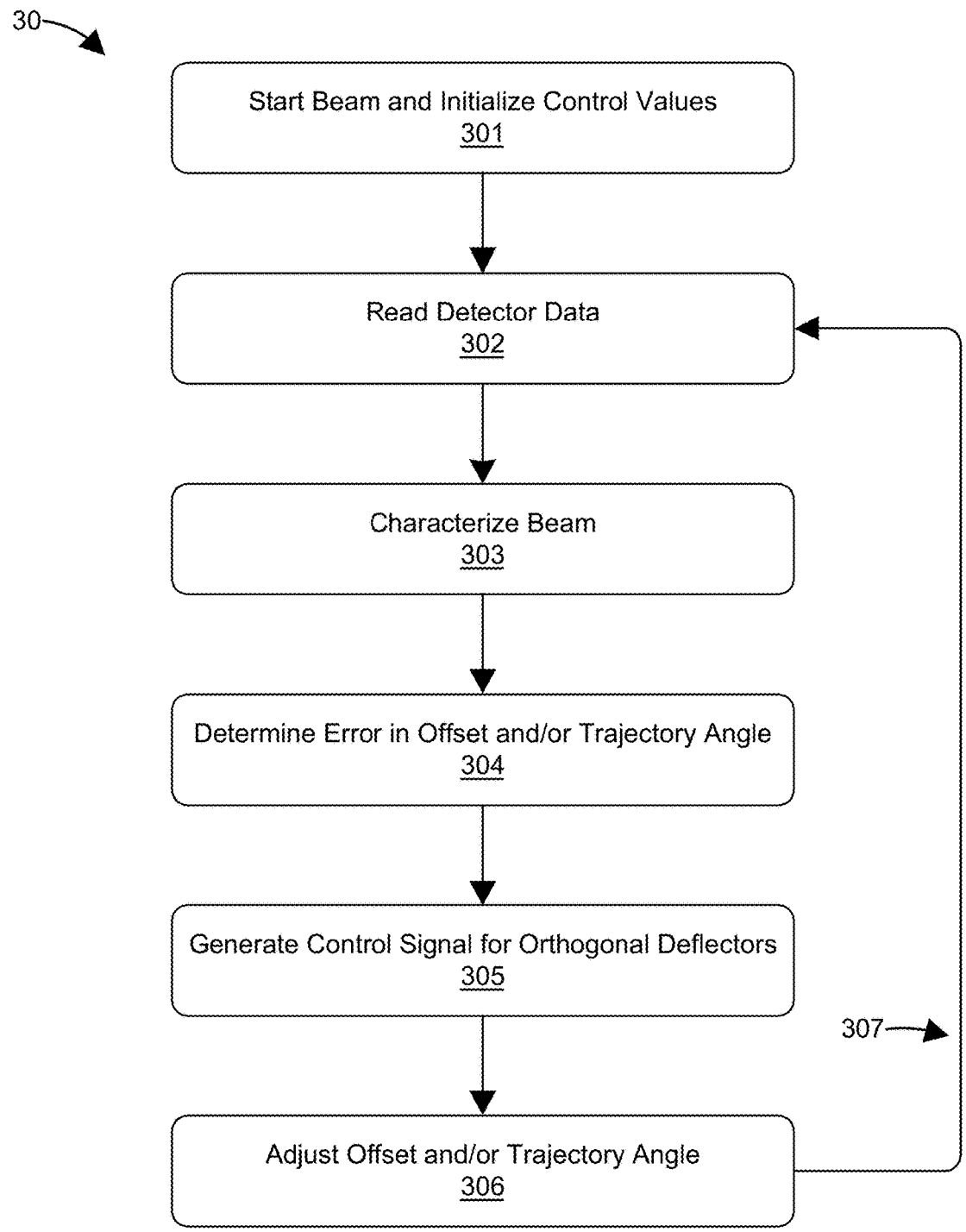
FIG. 3 is a flow chart illustrating a method for real-time trajectory correction of a charged particle pencil beam according to one or more embodiments.

FIG. 3 is a flow chart 30 illustrating a method for real-time trajectory correction of a charged particle pencil beam according to an embodiment. In step 301, the beam is generated at a desired offset, beam angle, and energy level. When the beam is first generated, the calibration and control parameters are initialized to zero as no correction control signals have been generated. Alternatively, the controller can generate initial control parameters for the beam based on historical data of control parameters used for the beam at the same energy level.

In step 302, the detector data output from first and second detector apparatus 250, 260 are read and collected through readout electronics. The readout electronics have sufficient bandwidth and processing speed to collect data at about 1 kHz or more.

In step 303, the controller characterizes the beam based on the data output from detector apparatus 250, 260. The characterization includes calculating the measured centroid position of the beam at each detector apparatus, which includes x and y position components as discussed above. The characterization also includes calculating the measured beam angle of the beam based on the measured centroid positions and the distance between corresponding detectors. The measured beam angle is used to determine the measured beam angles Θ (measured) and Φ (measured).

In step 304, the controller compares the characterized beam with a model beam to determine if any error correction is needed. The model beam has a model position or offset (x (model), y (model)) and a model beam angle, including model beam angles Θ (model) and Φ (model). As discussed above, the error calculation of the beam position or offset can be made using one of the measured positions at detectors 250/260 or using the projected offset of the beam at the isocenter plane, where a patient would be located during therapy. The model offset position can be scaled or adjusted based on the measured or projected position used for comparison. In general, the beam error can be defined by the following equations:

$$\Delta\Theta = \Theta(\text{measured}) - \Theta(\text{model})$$

$$\Delta\Phi = \Phi(\text{measured}) - \Phi(\text{model})$$

$$\Delta x = x(\text{measured or projected}) - x(\text{model})$$

$$\Delta y = y(\text{measured or projected}) - y(\text{model})$$

In step 305, the controller generates control signals to independently correct for the above errors in the parameters Θ, Φ, x, and y. The control signal can be generated based on a control algorithm, such as PI or PID, as discussed above.

In step 306, the control signals are sent to first and second orthogonal deflector apparatus 230, 240. First orthogonal deflector apparatus 230 can include a pair of electromagnets to adjust the x offset and/or the x beam angle Θ based on the control signals for those parameters. Likewise, second orthogonal deflector apparatus 240 can include a pair of electromagnets to adjust the y offset and/or the y beam angle Φ based on the control signals for those parameters. Electromagnets for first and second orthogonal deflector apparatus may be combined function magnets (e.g., multipole electromagnets) to reduce the total amount of space needed.

In some embodiments, the first orthogonal deflector apparatus 230 only adjusts the x offset and the second orthogonal deflector apparatus 240 only adjusts the y offset. Likewise, in some embodiments, the first orthogonal deflector apparatus 230 only adjusts the x beam angle Θ and the second orthogonal deflector apparatus 240 only adjusts the y beam angle Φ. Any combination of the above can also occur (e.g., the first orthogonal deflector apparatus 230 adjusts both the x offset and the x beam angle Θ while the second deflector apparatus 240 only adjusts the y beam angle y offset).

In step 307, the process returns to step 302 (read detector data) to characterize and adjust (if needed) the now-adjusted beam. Thus, the beam can be controlled in a closed loop and corrected iteratively and in real time. Since this process can occur without moving the patient, it can result in a significant savings in time and money, as discussed above.

In some embodiments, the beam adjustment parameters from each scan are stored in a memory. When the beam starts (step 301) and/or when the energy of the beam changes, the controller can use historical adjustment parameters (in the same scan run and/or over many scan runs over days, weeks, etc.) at the same energy level as the starting point for correcting the offset and/or beam angle of the beam. The historical adjustment parameters can provide a relatively good approximation for the necessary adjustment.

Figure 4:
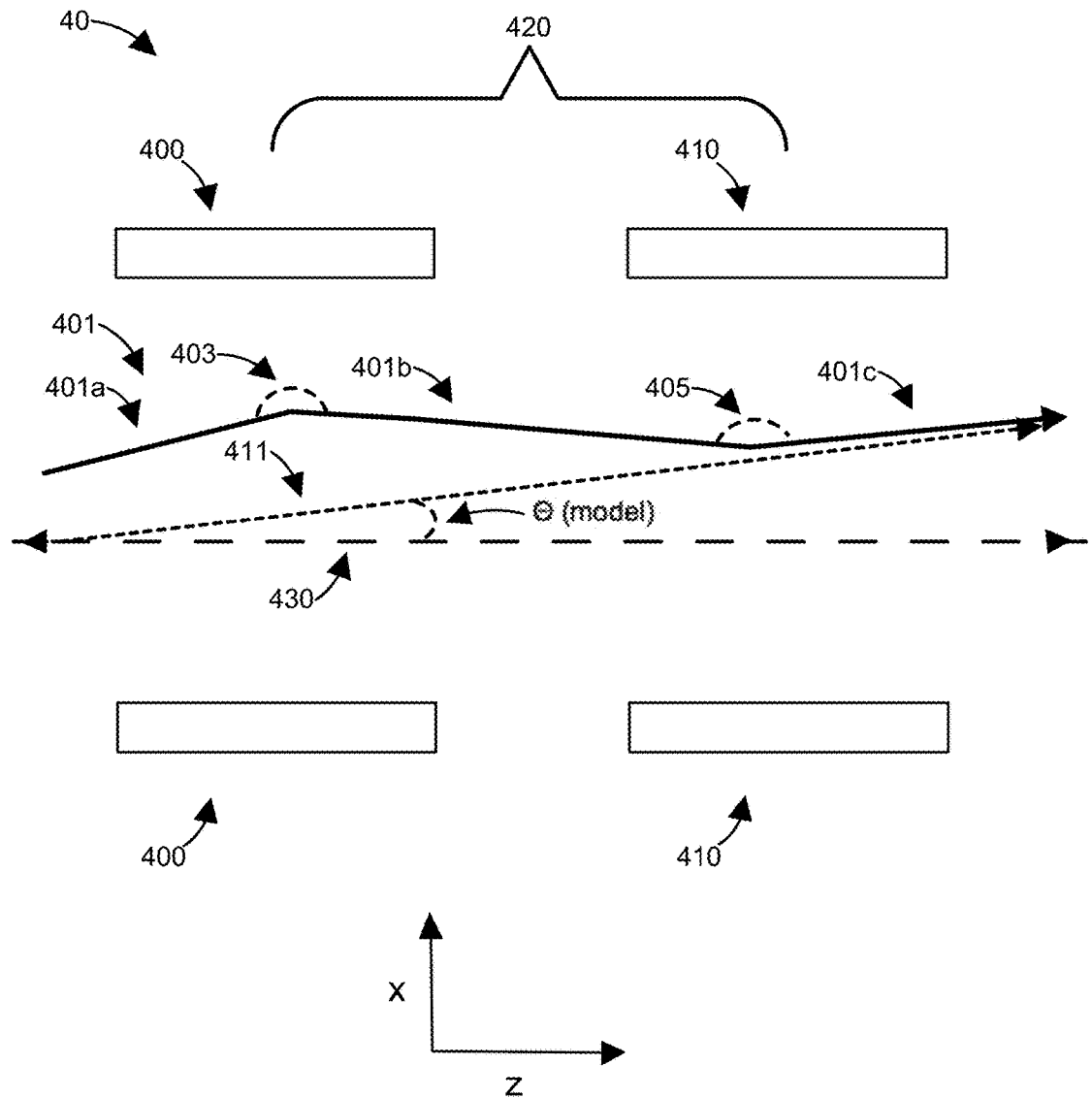
FIG. 4 is a side view of an orthogonal deflector apparatus according to one or more embodiments.

FIG. 4 is a side view of an orthogonal deflector apparatus 40 according to an embodiment. The orthogonal deflector apparatus 40 can be the same as first and/or second orthogonal deflector apparatus 230, 240, discussed above. The apparatus 40 includes first and second orthogonal deflector pairs 400, 410 separated by a distance 420, generally measured from the center of each deflector. The deflectors 400, 410 are configured to deflect the beam along a first axis (e.g., the x axis) orthogonal to an axis 430 parallel to the direction of travel of the beam (e.g., the z axis). The deflectors 400, 410 can provide a very good approximation of a discontinuous change in beam trajectory in the relevant axis (e.g., first axis) occurring at the longitudinal center (i.e., along the z axis) of each deflector magnet.

As illustrated, the first deflector pair 400 includes first opposing electromagnets that are aligned along a first axis parallel to the x axis. Similarly, the second deflector pair 410 includes second opposing electromagnets that are aligned along a second axis parallel to the x axis. The distance between the opposing electromagnets for each pair can be centered with respect to the nominal z axis.

In operation, the deflectors 400, 410 work together to adjust the x offset and/or the x beam angle Θ of beam 401. In some embodiments, the deflectors 400, 410 only need to deflect the beam by a few milliradians to correct the offset and beam angle. The first orthogonal deflector 400 receives a first control signal from controller 270 to adjust the x offset of beam 401a. In response to the first control signal, the first orthogonal deflector 400 generates a first magnetic field, orthogonal to the z axis, to deflect the beam laterally at a first beam angle 403. The first beam angle 403 is selected so that deflected beam 401b is at the model x offset of model beam 411 when the deflected beam 401b travels distance 420 to reach the second orthogonal deflector 410.

The second orthogonal deflector 410 receives a second control signal from controller 270 to adjust the beam angle Θ of beam 401. In response to the second control signal, the second orthogonal deflector 410 generates a second magnetic field, orthogonal to the z axis, to deflect the deflected beam 401b at a second beam angle 405. The second beam angle 405 is selected so that corrected beam 401c is at the model beam angle Θ (model) of model beam 411. The beam angles Θ and Φ can be measured with respect to the z axis or a line parallel to the z axis.

Although deflectors 400 and 410 are each illustrated as having a pair of magnets, it is noted that other deflectors 400, 410 can have other configurations. For example, one or both deflectors 400, 410 can include a magnet in the shape of a toroid, annulus, or other shape as known in the art. In another example, deflectors 400, 410 can include quadrupole, sextupole, or octopole magnetic deflectors where two dipoles are effectively superimposed as a "combined function" electromagnet which can reduce the longitudinal footprint of the deflectors. An example of a sextupole and an octopole magnetic deflector can be found in U.S. Pat. No. 8,378,312, entitled "System, Apparatus and Method For Deflecting a Particle Beam," which is incorporated herein by reference. The '312 patent is assigned to the same assignee as this application.

As illustrated in FIG. 4, orthogonal deflector apparatus 40 is configured to correct the x offset and/or the x beam angle Θ of beam 401. However, it is noted that the configuration of orthogonal deflector apparatus 40 in FIG. 4 is exemplary and other configurations are possible. For example, orthogonal deflector apparatus 40 can be configured to adjust the y offset and/or the y beam angle Φ of beam 401, or any other offset and/or beam angle depending on the relevant coordinate system. Accordingly, when orthogonal deflector apparatus 40 is configured to correct the x offset and/or the x beam angle Θ (i.e., in the exemplary embodiment illustrated in FIG. 4), orthogonal deflector apparatus 40 can be the same first orthogonal deflector apparatus 230 discussed above. Similarly, when orthogonal deflector apparatus 40 is configured to correct the y offset and/or the y beam angle Φ, orthogonal deflector apparatus 40 can be the same as second orthogonal deflector apparatus 240 discussed above. Of course, the order of first and second deflector apparatus 230, 240 can be switched in which case orthogonal deflector apparatus 40 as configured to correct the x offset and/or the x beam angle Θ can correspond to second orthogonal deflector apparatus 240 and orthogonal deflector apparatus 40 as configured to correct the y offset and/or the y beam angle Φ can correspond to first orthogonal deflector apparatus 230.

One skilled in the art will also recognize that a pair (or more) of orthogonal deflector apparatus 40, 40' (e.g., corresponding to first and second deflector apparatus 230, 240 and/or x and y axes) can include intermingled or interleaved components. For example, the first orthogonal deflector 400 of deflector apparatus 40 can be disposed adjacent first orthogonal deflector 400' of deflector apparatus 40. Likewise, second orthogonal deflector 410 of deflector apparatus 40 can be disposed adjacent first orthogonal deflector 410' of deflector apparatus 40. In other words, the deflectors can be disposed as first orthogonal deflector 400 (corrects x offset) followed by first orthogonal deflector 400' (corrects y offset), followed by second orthogonal deflector 410 (corrects x beam angle Θ), followed by second orthogonal deflector 410' (corrects y beam angle Φ). Of course, the deflectors can also be disposed in the opposite order: first orthogonal deflector 400' (corrects y offset) followed by first orthogonal deflector 400 (corrects x offset), followed by second orthogonal deflector 410' (corrects y beam angle Φ), followed by second orthogonal deflector 410 (corrects x beam angle Θ). Those skilled in the art will recognize that other combinations and orders of the deflectors are possible.

In general, the deflectors 400, 410 can have a fast action and a predictable response with minimal hysteresis. For example, the deflectors 400, 410 can be designed to be as low in inductance as practical, and having laminated or ferrite return yokes.

Figure 5:
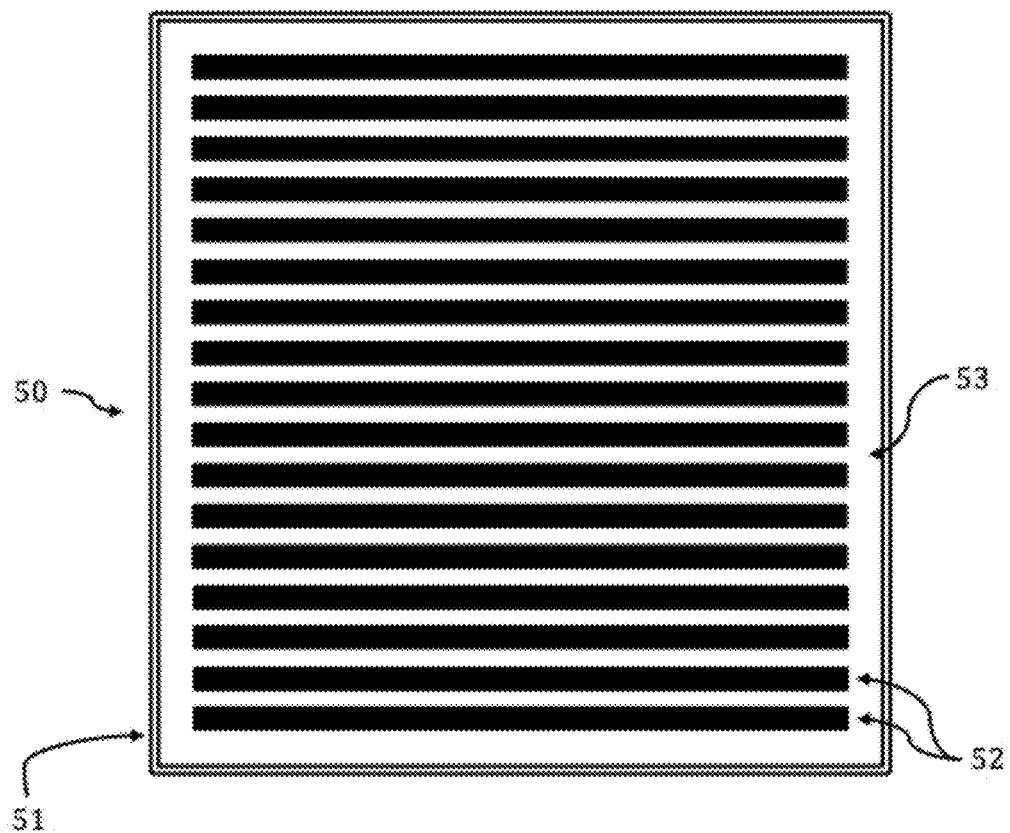
FIG. 5 illustrates a strip electrode assembly according to one or more embodiments.

FIG. 5 illustrates a strip electrode assembly 50 according to an embodiment. Strip electrode assembly 50 includes frame 51, film 53 and field strips 52. Assembly is performed by bonding tensioned film 53 to frame 51. Film 53 is aluminized polyimide and can have a thickness of about 25 mm or less in some embodiments (about 8.5 mm to about 12.5 mm, in one or more embodiments). However, other metalized polymers (e.g., Mylar, aluminum/gold/nickel coated polyimide/polyamide) can also be used. Frame 51 is made of aluminum or other suitable rigid material. As used herein, "about" means plus or minus 10% of the relevant value. It is noted that strip assembly 50 is provided to illustrate an exemplary embodiment of a PBS system.

As with all the disclosed electrode structures, vertical strip electrode assembly 50 is radiation resistant to prevent degradation. The electrode structures must also be as thin as possible to minimize scattering of the beam as it passes through the ionization chamber and energy loss in the detector. Field strips 52 are fabricated from pre-aluminized polymer film. In a preferred embodiment, the polymer is polyimide which is extremely radiation-resistant. The strength of polyimide also allows film 53 to be sufficiently thin, for example less than or equal to about 10 microns in some embodiments, and thus does not contribute significantly to beam scatter or energy loss. In some embodiments, the thickness of the metal on the metalized polymer film 53 is less than or equal to about 1,000 Å.

The film 53 is stretched so it remains under tension during fabrication, and during use. The advantage of processing the film in its stretched state is that no distortion is added in post-processing. If the film were patterned then stretched, the pattern would be modified and the precision compromised.

The number of field strips 52 can range from 16 to 128, depending on spatial resolution. Field strips 52 are created by selectively removing the aluminum from film 53 to create a number of isolated electrodes on the insulating polymer substrate comprised by film 53. In one embodiment, the removal is performed using laser ablation. In this process, a highly-focused, nanosecond pulsed ultra-violet (UV) laser is directed onto the metal film surface. With sufficient energy density, the pulsed laser light vaporizes the metal film over an area of a few to tens of microns, leaving the substrate largely intact. The technique is capable of very high spatial accuracy, typically on the scale of a few microns. The process does not require mechanical contact with the film. Unlike alternative methods such as lithography, the material does not need to be coated, stripped, etched, etc., all of which can damage or distort the electrode film.

As part of the laser processing, alignment holes (not shown) are cut into film 53. These are precisely aligned with the electrode pattern. During the final assembly, these fiducial holes or markings are used to register film 53 with the support structure through the use of dowel pins. These same holes are then used to align the intermediate support structure with the overall support structure. In this way, the laser-ablated pattern can be aligned with the mechanical shell with an accuracy of less than or equal to about 10 microns.

Figure 6:
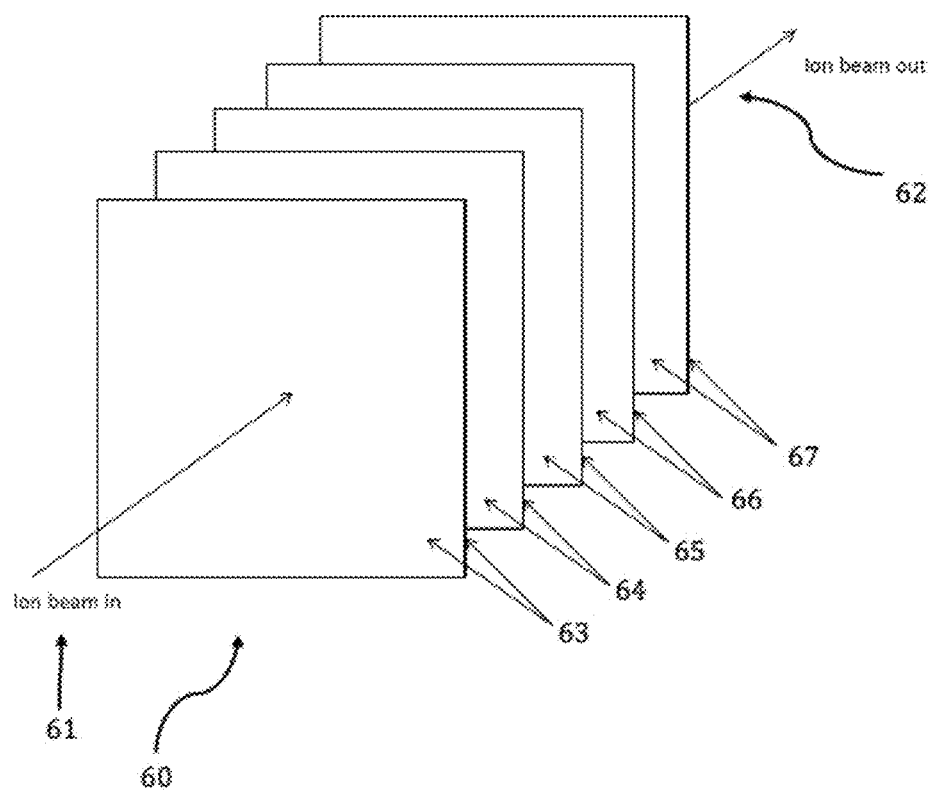
FIG. 6 illustrates an abstraction of a strip ionization chamber sub-assembly according to one or more embodiments.

FIG. 6 illustrates an abstraction of a strip ionization chamber sub-assembly 60 according to an embodiment. Ionization chamber sub-assembly 60 comprises ground planes 63, 67, high voltage (HV) electrodes 64, 66, and X-Y readout electrode 65. X-Y readout electrode 65 is a structure comprising X field strips and Y field strips, such as strip electrode 50 (in different orientations), on opposite sides, thereby minimizing the number of necessary electrodes. HV electrodes are biased relative to grounded X-Y readout electrode thereby producing an electrostatic field with field lines similar to that of a parallel plate capacitor. In operation, particle beam 61 ingresses ionization chamber sub-assembly 60 through ground plane 63.

A gas gap disposed between HV electrode 64 and X-Y readout electrode 65 gives rise to an active region associated with an ionization event. Gas molecules in the active region become ionized after being struck by particle beam 61. Consequently, electrons and negative ions are pulled toward and collected by the HV electrode 64 (assuming a positive voltage is applied to HV electrode 64). Conversely, positive ions are drawn into the grounded X-Y readout electrode 65, pursuant to the Lorentz force albeit with thousands of small scattering events which limit velocity. If the voltage polarity of the HV electrode 64 is reversed (i.e., if a negative voltage is applied to HV electrode 64), positive ions would be pulled toward the HV electrode 64 and negative ions and electrons would be drawn to and collected by the X-Y readout electrode 65.

Similarly, a gas gap disposed between HV electrode 66 and X-Y readout electrode 65 gives rise to an additional active region. Gas molecules in the active region become ionized after being struck by particle beam 61, after passing through X-Y readout electrode 65. Subsequently, cations are pulled toward the HV 66 which acts as the cathode. Consequently, electrons and negative ions are pulled toward and collected by the HV electrode 66 (assuming a positive voltage is applied to HV electrode 66). Conversely, positive ions are drawn into the grounded X-Y readout electrode 65, pursuant to the Lorentz force albeit with thousands of small scattering events which limit velocity. If the voltage polarity of the HV electrode 66 is reversed (i.e., if a negative voltage is applied to HV electrode 66), positive ions would be pulled toward the HV electrode 66 and negative ions and electrons would be drawn to and collected by the X-Y readout electrode 65.

HV electrodes 64, 66 are made from unpatterned metalized polyimide, although they may be made from any suitably radiative resistant material (rad hard) exhibiting bulk conductivity. In an alternate embodiment, a single, two-sided HV plane replaces the X-Y readout electrode 65 and vertical and horizontal electrodes (faced accordingly) replace HV electrodes 64, 66.

The strip electrode assembly 50 and/or the strip ionization chamber sub-assembly 60 can be used in system 20 or method 30 (and/or in the systems described below), such as in first and/or second detector apparatus 250, 260 discussed above. Strip electrode assembly 50 and strip ionization chamber sub-assembly 60 are further described in U.S. patent application Ser. No. 14/215,311, which is hereby incorporated by reference, as discussed above. One skilled in the art will recognize that additional configurations of the PBS system are possible in system 20 and/or method 30, including different ionization chambers than those described herein or replacing the disclosed ionization chambers with other position-sensitive detectors.

Figure 7:
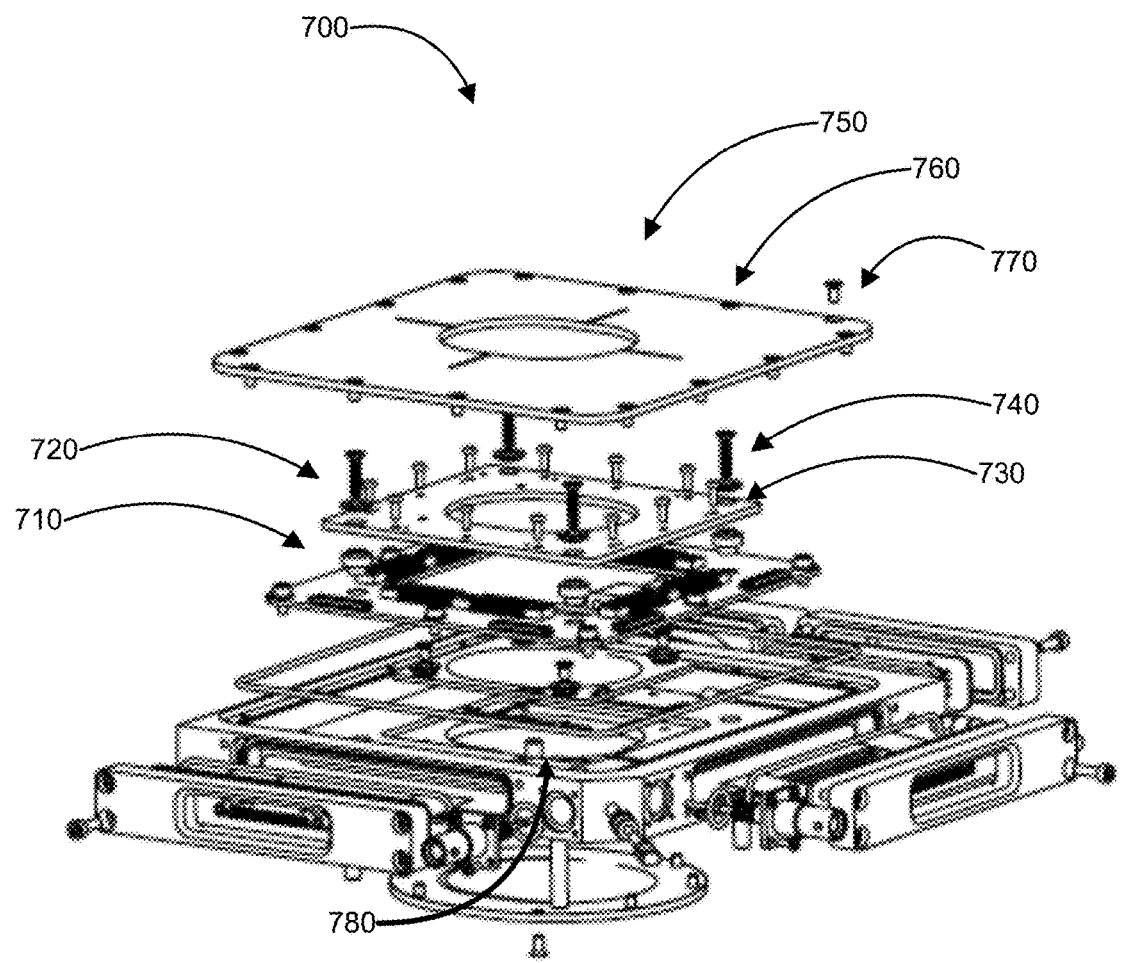
FIG. 7 illustrates an exploded perspective view of a pixelated detector according to one or more embodiments.

FIG. 7 illustrates an exploded perspective view of a pixelated detector 700 according to an embodiment. The detector 700 includes an ablated (or pixelated) electrode material 710 bonded to a support plate 720. The support plate 720 can be a rigid insulating substrate, such as FR4 fiberglass, or a metal plate (e.g., nickel-plated aluminum), depending on the need to maintain electrical isolation on the bonded surface. The support plate 720 can be mounted on the ablated electrode material 710 utilizing fiducial structures 730 and alignment pins 740 to provide mechanical alignment between the ablated pattern and the support plate 720, which can provide an accuracy greater than about 25 microns.

The support plate 720 is disposed in an instrument case 750 using fiducial structures 760 and dowel pins 770 to maintain a high degree of mechanical alignment between the electrode pattern 710 and the instrument case 750.

A bias electrode 780 is fabricated in a similar manner, without the need for any patterning. The bias electrode 780 is mounted in the instrument case 750 with high-precision spacers to maintain a stable and accurate gas layer between the two electrode layers. The gas layer can include or can be air.

Figure 8:
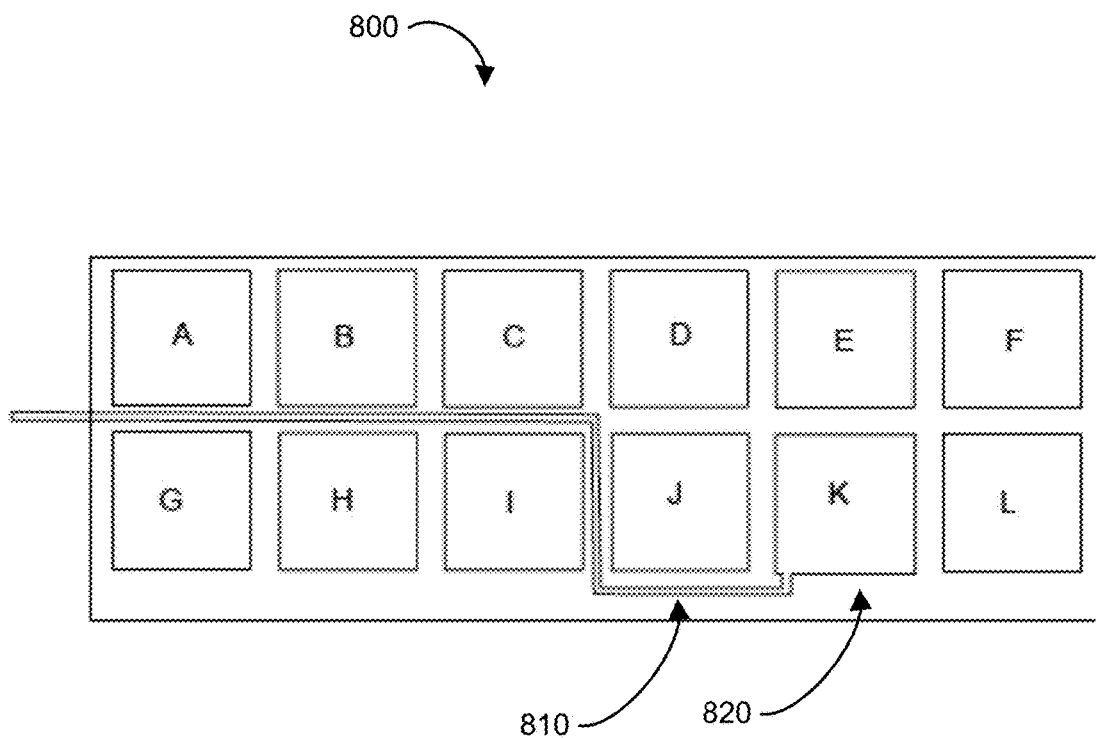
FIG. 8 illustrates an array of pixels according to one or more embodiments.

FIG. 8 illustrates an array of pixels 800 according to an embodiment. The array of pixels 800 can be disposed in ablated electrode material 710. For illustration purposes, a front side trace 810 for a single pixel (K) 820 is shown for clarity. Back side traces are also possible using plated through holes to connect the pixel to the trace.

The pixelated detector 700 and/or the pixel array 800 can be used in system 20 or method 30, such as in first and/or second detector apparatus 250, 260 discussed above. Pixelated detector 700 and/or Pixel array 800 are further described in U.S. patent application Ser. No. 14/493,098, which is hereby incorporated by reference, as discussed above.

Figure 9:
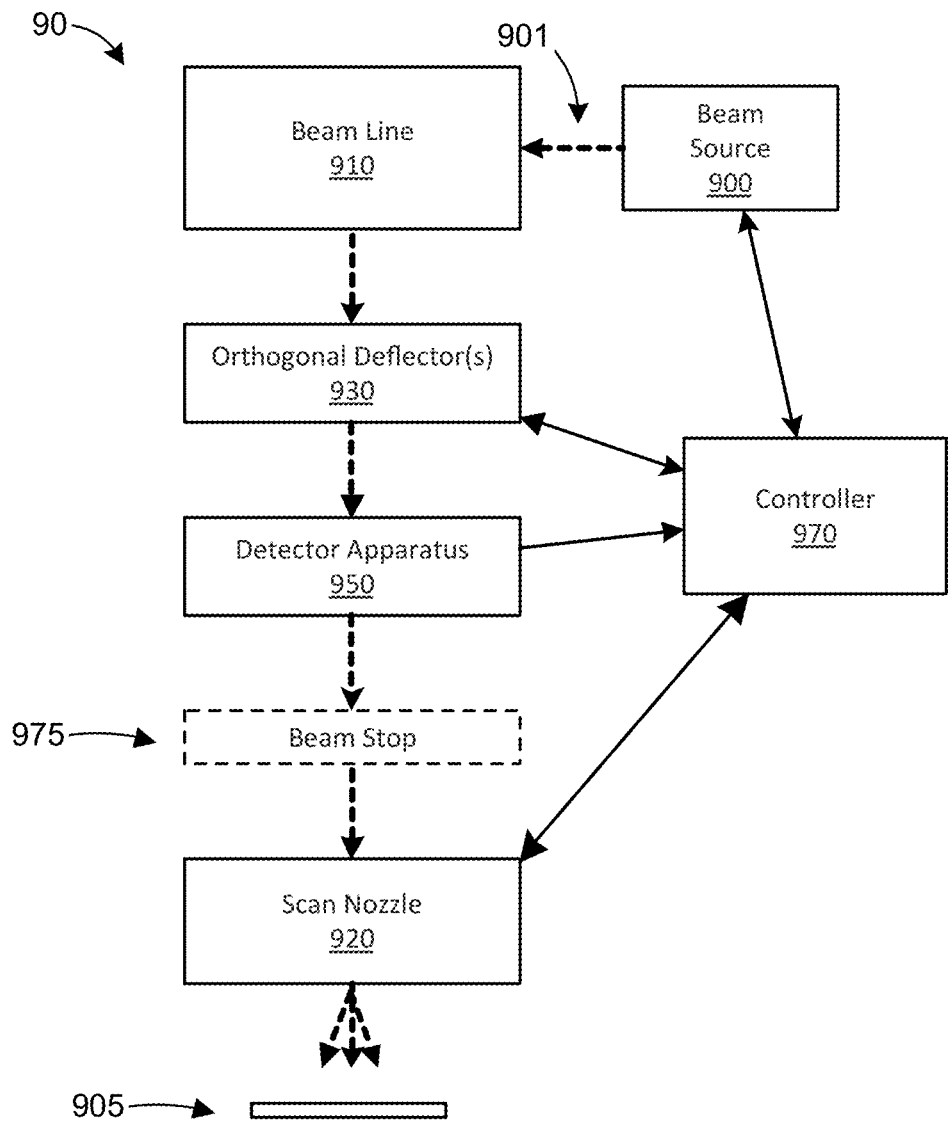
FIG. 9 illustrates a pencil beam system according to one or more embodiments.

FIG. 9 illustrates a PBS system 90 according to an embodiment. The system 90 includes beam source 900, beam line 910, orthogonal deflector(s) 930, detector apparatus 950, controller 970, and optional beam stop 975. Beam source 900 and beamline 910 can be the same as or different than beam source 100/200 and beamline 110/210 described above. Isocenter plane 905 is illustrated for reference.

PBS system 90 is a simplified embodiment of PBS system 20 described above. In PBS system 90, only the offset correction parameters are controlled by controller 970.

Detector apparatus 950 measures the two-dimensional position (e.g., (x, y) position) of beam 901, similar to first and second detector apparatus 250, 260 discussed above. For example, detector apparatus 950 can include a pixelated detector or a pair of strip detectors. Controller 970 compares the measured x and y positions of beam 901 with model x and y positions of a model beam to determine an offset error, as described above. Controller 970 then generates a control signal to correct the x and/or y components of the offset error. The control signal is sent to orthogonal deflector(s) 930.

Orthogonal deflector(s) 930 generate magnetic fields to adjust the trajectory of beam 901. Orthogonal deflector(s) 930 can independently adjust the x and y components of beam 901 trajectory. For example, orthogonal deflector(s) 930 can include a first pair of correction magnets to adjust the x component of beam 901 trajectory and a second pair of correction magnets to adjust the y component of beam 901 trajectory. Each pair of correction magnets can be the same as orthogonal deflectors 400 or orthogonal deflectors 410 discussed above. Alternatively, orthogonal deflector(s) 930 includes a multipole electromagnet that provides a combined function of correcting the x and y components of beam 901 trajectory.

After passing through orthogonal deflector(s) 930, the trajectory of beam 901 is corrected to compensate for the measured offset error. It is recognized that the beam angle will have to be adjusted to correct the measured offset error of beam 901.

As can now be appreciated, the present disclosure provides improved control systems and methods for controlling a charged particle pencil beam system. The control system includes first and second ionization chambers to detect the position and beam angle of the beam at two locations along the beam path. The measured position and beam angle are compared with a model position and beam angle to determine an offset error and a beam angle error in the beam. A first pair of orthogonal correctional magnets can be used to modify the beam path to reduce the "x" component of the offset and beam angle errors. A second pair of orthogonal correctional magnets can be used to modify the beam path to reduce the "y" component of the offset and beam angle errors. Thus, the control system provides up to four degrees of freedom to control the beam in real time during therapy.

Another aspect of the disclosure is directed to a low-inductance, low-power compensation magnet assembly that can be used to fine tune or spread a charged particle pencil beam in a charged particle pencil beam system. The compensation magnet assembly is disposed upstream (e.g., immediately upstream) of the scan nozzle such that the charged particle pencil beam passes through the compensation magnet assembly before it passes through the scan nozzle. The compensation magnet assembly and its feedback loop have a faster response rate than the scan nozzle and its feedback loop, thus allowing the compensation magnet assembly to fine tune or spread the beam.

Figure 10:
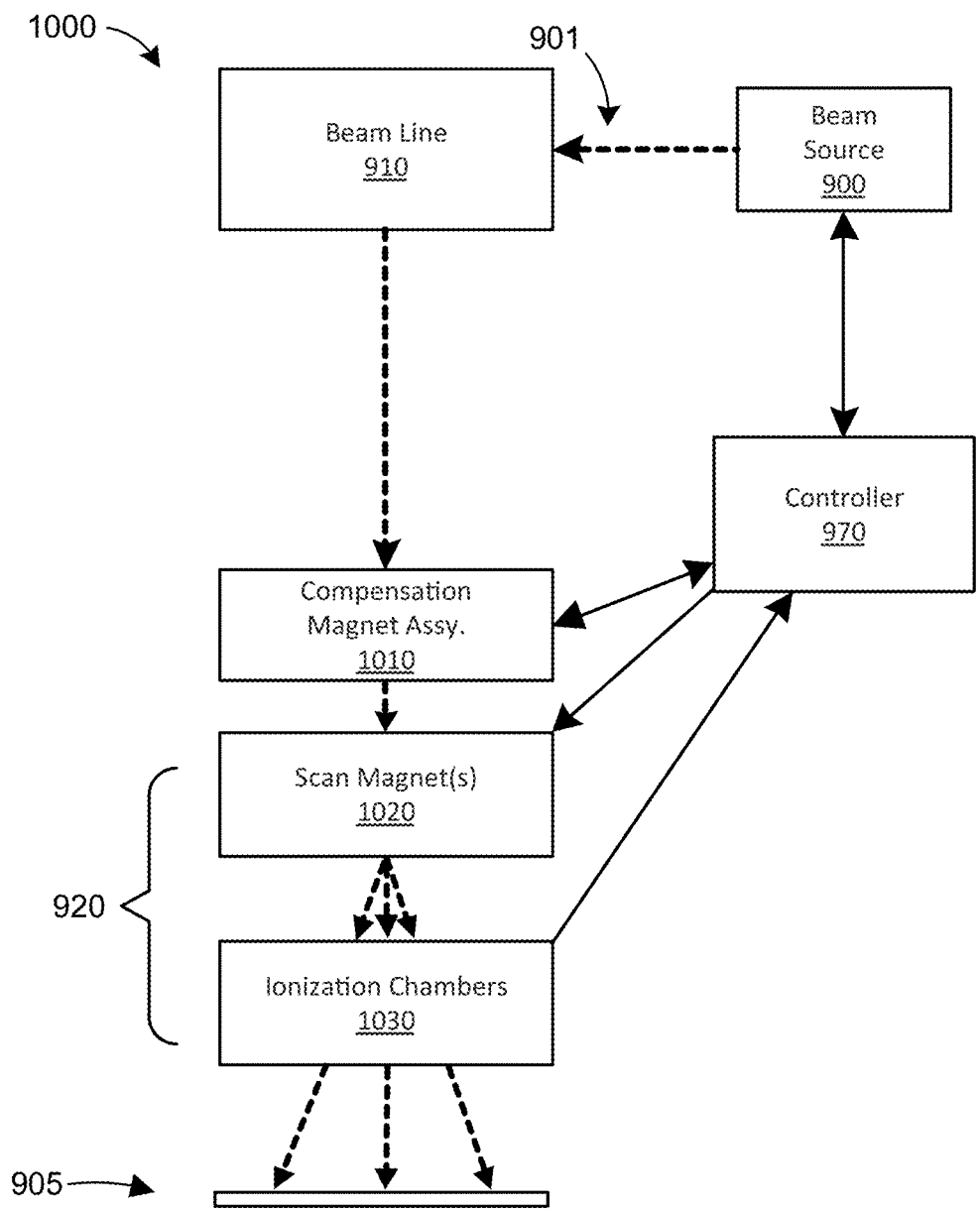
FIG. 10 illustrates a pencil beam system including a compensation magnet assembly associated with the beam scan magnet(s) according to one or more embodiments.

FIG. 10 illustrates a pencil beam system 1000 that includes a "fine tuning" or "compensation" magnet assembly 1010 (in general, compensation magnet assembly 1010) that is associated with beam scan magnet(s) 1020 of main scan nozzle assembly 920. The compensation magnet assembly 1010 may be disposed anywhere upstream (before) the main scan nozzle 920 (which includes one or more scan magnet(s) 1020 and ionization chambers 1030) in the pencil beam scanning system described earlier. In the embodiment illustrated in FIG. 10, the compensation magnet 1010 is located just before the scan magnet(s) 1020.

The compensation device or mechanism or means 1010 may comprise one or more low inductance electromagnets (e.g., about 50 μH to about 2 mH, including about 150 μH, about 500 μH, about 1,000 μH, and about 1,500 μH), configured and arranged to deflect a charged particle (proton) pencil beam in a plurality of dimensions, e.g., in a plane orthogonal to (or substantially orthogonal to) the direction of the beam. In some embodiments, the compensation magnet assembly 1010 includes a single combined function electromagnet, such as a multipole electromagnet, for example to minimize its insertion length or footprint along the beam axis. In other embodiments, the compensation magnet assembly 1010 includes a first pair of electromagnets to deflect the charged particle pencil beam in a first direction (e.g., along the "x" axis) that is orthogonal to the direction of travel of the charged particle pencil beam (e.g., the "z" axis) and a second pair of electromagnets to deflect the charged particle pencil beam in a second direction (e.g., the "y" direction) that is orthogonal to the direction of travel of the charged particle pencil beam and that is orthogonal to the first direction.

The low inductance electromagnet arrangement used to compensate the beam may be of modest physical size and have a moderate power consumption, intended to achieve modest deflections or compensations in the beam, for example on the order of a millimeter or a maximum of a centimeter in some examples, measured at the isocenter plane 905. In a specific embodiment, the compensation magnet assembly 1010 limits the maximum possible deflection or compensation of the beam of about 3 mm to about 4 mm at the isocenter plane, which corresponds to a deflection angle of about 0.13 degrees (or about 2.2 mrad) for 230 MeV protons when the compensation magnet assembly 1010 is positioned at about 1,800 mm from isocenter, which corresponds to just before the main scan magnets 1020 in some systems. It is noted that the typical energy range for proton therapy is 70 MeV to 230 MeV. The beam rigidity (i.e., ease of deflection) changes by a factor of 1.89 over this range. Thus, if the compensation magnet assembly 1010 can provide a deflection angle of about 2.2 mrad at 230 MeV, it can also provide a deflection angle of about 2.2 mrad×1.89=4.16 mrad at 70 MeV. A limited capacity to deflect or compensate the beam (e.g., over about 3 mm to about 4 mm at isocenter at 230 MeV) can prevent the compensation magnet assembly 1010 from making a large change in beam position in the event of a fault or other system error, which can protect the patient from unintentional exposure to proton therapy.

However, the compensation electromagnet assembly is capable, due to this design, of rapid changes so as to quickly move the beam about within this limited compensatory range. For example, the relatively small size, small inductance, and moderate maximum magnetic field strength of the compensation magnet assembly 1010 enable a faster response rate (e.g., about 5 to about 10 times faster) than the scan magnet(s) 1020. In some embodiments, the inductance of the compensation magnet assembly 1010, as seen by its power supply, can be the primary influence on the response rate. This inductance can be kept low by (a) keeping the total magnetic field energy low (e.g., a small volume of modest flux density); and (b) reducing the number of coil turns. The inductance is proportional to the square of the number of coil turns (e.g., $N^2$), so reducing the number of coil turns can have a large impact on the inductance. For example, 2,400 ampere-turns of magnetizing force can be generated with 100 A of current through 2 coils each with 12 turns.

An example of the structure of a compensation electromagnet 1700 in compensation magnetic assembly 1010 is illustrated in FIG. 17. The compensation electromagnet 1700 includes 4 coils 1710 wrapped around a return yoke 1720. The coils 1710 are in a racetrack configuration with 12 turns on each coil 1710 and a maximum current of 100 A. The coils 1710 can be wound from a hollow conductor material (the bore is the water-cooling channel). A single layer of conductor material can be disposed on each coil which minimizes AC losses for use in a blurring or spreading application, as discussed herein. The coils 1710 are arranged in pairs, with a first pair 1710A, 1710B configured to deflect the beam horizontally (e.g., along the X axis) as illustrated in FIG. 17, and a second pair 1710C, 1710D configured to deflect the beam vertically (e.g., along the Y axis) as illustrated in FIG. 17

The return yoke 1720 has a "window frame" configuration and can be formed of ferrite or powdered iron or it can be formed of thin laminated silicon steel. In an example, the return yoke 1720 is formed of MN60 (Mn—Zn ferrite), available from Ceramic Magnetics, Inc. of Fairfield, N.J. The return yoke 1720 can be about 100 mm long (e.g., along an axis passing into the page of FIG. 17) and the clear bore 1730 for the beam can have a cross-sectional area of about 60 $mm^2$. The beam could pass through the bore 1730 in a non-conducting vacuum pipe, in air, or in helium.

The speed at which an electromagnet can be slewed from one field setting to another can be limited by the available power supply voltage, which cannot be made arbitrarily large for reasons of cost, safety and reliability. The slewing speed of the coil current (which to first order determines the field slewing) is given by $dI/dt=(V-iR)/L$. Coil resistance R can be made rather small in an electromagnet, so resistive voltage iR is small and the speed is primarily set by available voltage V and the inductance L. In a specific example, the compensation magnet assembly 1010 can have L=150 μH, R=9 mohm, and a 100 A power supply. In this example, the resistive voltage iR is at most 0.9V and can be almost ignored since the power supply can have, for example, 100 V voltage compliance.

In some embodiments, the current control loop of the power supply for the compensation magnet assembly 1010 can operate at maximum speed (thus minimum ringing or undershoot when settling to a new current setting) when the load is purely resistive, whereas inductance introduces phase shifts that must be compensated and inevitably reduces the overall speed of response. As such, reducing the inductance of the compensation magnet assembly 1010 (e.g., the electromagnets) increases the overall speed of response.

The relatively small maximum magnetic field strength of the compensation assembly and its relatively small maximum deflection angle enable its operation with minimal hysteresis or eddy currents. The relatively small maximum magnetic field strength also allows the field return yoke to be constructed from ferrite material, powdered iron, or thin laminated silicon steel which have negligible eddy currents. Ferrite cannot be typically used in the main scan magnet(s) 1020 because the yoke magnetic fields are too high for the material so it fully saturates which is undesirable. In some embodiments, the compensation electromagnet assembly 1010 has a maximum magnetic field strength of about 400 Gauss or about 300 Gauss to about 500 Gauss. This is significantly lower than the maximum magnetic field strength of a typical scan magnet (e.g., scan magnet(s) 1020), which is about 5,000 Gauss to about 10,000 Gauss. Thus, the maximum magnetic field strength of the compensation electromagnet assembly 1010 can be about 10× to about 25× lower than the maximum magnetic field strength of scan magnet(s) 1020.

It is noted that compensation electromagnet assembly 1010 can be deployed independently of the trajectory correction apparatus and methods described above. Thus, some embodiments include only include compensation electromagnet assembly 1010 and other embodiments include only the trajectory correction apparatus/methods described above. Still other embodiments include both compensation electromagnet assembly 1010 and the trajectory correction apparatus/methods described above.

The compensation electromagnet assembly 1010 can be used to (a) correct the beam position within its limited deflection range by adjusting the beam trajectory; (b) reduce scan system settling time; (c) compensate for hysteresis in the scan system; and/or (d) blur/spread the beam spot to increase the effective beam spot size.

In one instance, a fast feedback loop circuit can control the compensation magnet assembly 1010, which receives as an input the pencil beam spot position (e.g., from a position sensor in the isocenter plane or other plane through which the beam passes). For example, in FIG. 10 the controller 970 receives the output signals from ionization chambers 1030, which indicate the position (e.g., a centroid position) of the beam 901 in the plane of each ionization chamber 1030. In some embodiments, the controller 970 can determine a projected position of the beam 901 in the isocenter plane 905, for example based on at least two detected positions of the beam 901 and the known locations of the ionization chambers. Alternatively, the controller 970 can determine the projected position of the beam 901 in the isocenter plane 905 using one detected position of the beam 901 and the assumption that beam 901 deflects at the known longitudinal center of the respective scan magnet(s) 1020.

The controller 970 can compare the detected position(s) and/or the projected position of the beam 901 with corresponding one or more target positions and/or a projected target position and can adjust the compensation magnet assembly 1010 accordingly. Thus, the compensation magnet assembly 1010 can provide real-time correction (or approximately real-time correction) of the beam position (e.g., by adjusting the beam trajectory), compensation for magnet hysteresis of scan magnet(s) 1020, and/or compensation for scan magnet(s) 1020 amplifier response.

In general, the foregoing feedback loop (i.e., ionization chambers 1030, controller 970, and compensation magnet assembly 1010) has a faster response rate than the feedback loop for the scan magnet(s) 1020 (i.e., ionization chambers 1030, controller 970, and scan magnet(s) 1020). In some embodiments, the compensation magnet assembly feedback loop, including compensation magnet assembly 1010, has a response rate of at least 2 times, at least 4 times, at least 6 times, at least 8 times, and/or at least 10 times as fast as the response rate of the scan magnet(s) feedback loop. The faster response rate of the compensation magnet assembly feedback loop can allow the compensation magnet assembly 1010 to provide the foregoing compensation(s)/correction(s) at or near real time (e.g., faster than the response rate of the scan magnet(s) feedback loop). In some embodiments, the compensation magnet assembly 1010 is designed to have a limited amount of available correction for beam 901 to prevent the correction from going out of control. For example, the compensation magnet assembly 1010 can only deflect the beam 901 by a millimeter up to a maximum of a centimeter, measured at the isocenter plane, as discussed above.

The response rate of the scan magnet(s) 1020 can be determined by its inductance as noted earlier, by practical and economic constraints on its power supply and coil design, by eddy currents in its yoke when the magnetic field is changed, by the phase lags due to the inductive nature of the load, by the loop response of the power supply, and/or by the switching rate of the power supply (high current supplies are generally switch-mode topology). By designing a compensation magnet that does not have to solve the whole scan magnet design problem, which is to deflect the beam over a large range of angles, but rather only a small part of the problem (e.g., deflect the beam over about 1% of the range of the scan magnet(s)), we can alleviate some or all of the scan system challenges and produce a composite system where the compensation magnet can be much faster in its limited range of operation. For example, the increased response rate of the compensation magnet can be provided by its low inductance, as discussed above. In another example, the return yoke of the compensation magnet can be made of ferrite, powdered iron, or thin laminated silicon steel to eliminate eddy currents. In another example, the power supply of the compensation magnet can have lower current and/or voltage which can provide a higher control loop speed. All combinations of the foregoing examples are possible (e.g., the compensation magnet can have low inductance, a return yoke made of ferrite, powdered iron, or thin laminated silicon steel and/or a power supply with a lower current and/or voltage).

Thus, the compensation magnet assembly 1010 allows the controller 970 to fine tune/correct the beam position during the longer response period required to adjust the beam positon using scan magnet(s) 1020, which may be offset due to magnet hysteresis of scan magnet(s) 1020 and/or due to scan magnet(s) 1020 amplifier bandwidth limitations, which may limit the time it takes to settle after a slew in the inductive load response. The compensation magnet assembly 1010 can also be used to spread the beam spot over an area (e.g., from about 1 mm to about 10 mm of the target, about 5 mm, or any value or range therebetween) at the isocenter plane to provide dosage to a larger area of the patient, thus improving the efficiency of the system. Examples of the fine tuning, adjustment, and beam spread that can be performed by compensation magnet assembly 1010 are illustrated in FIGS. 11-13.

In another instance, sampling the magnetic field of the main scan magnet(s) 1020 can be used to control the compensation magnet assembly 1010. For example, the magnetic field of the scan magnet(s) 1020 can be measured with one or more Hall probes to determine the total magnetic field integral seen by an ion passing through the scan magnet(s) 1020. This can provide an indication of how the magnetic field changes as the scan magnet(s) 1020 setting is changed. In general, the scan magnet(s) 1020 have a non-ideal response to changes in its setting (e.g., it takes time to slew the inductance, the coil current may over or undershoot due to limitations of power supply control loop when driving the inductive load, and/or the field may not settle even when the current is settled due to eddy currents). If these effects are systematic, then the compensation magnet assembly 1010 can compensate for them to produce a near-ideal response either by an open loop correction waveform, or through measurement of the magnetic field and minimization of the error via a servo control. For very small changes, the compensation magnet assembly 1010 could even "hide" the scan magnet inductance slewing time if the required spot position movement is within the limited range (or maximum deflection angle) of the compensation magnet assembly 1010.

In yet another instance, a feed forward program derived from a record of the recent scan magnet history is used as an input to control the compensation magnet assembly 1010. A combination of the sampling and feed forward controls is also possible in some embodiments.

In an aspect, the aforementioned compensation magnet assembly can be used to compensate the limited current control loop bandwidth of the scan magnet power supplies, which can be achieved using similar means as described above with respect to compensate for hysteresis in the PBS system.

In another aspect, the orthogonal deflector(s) 930 illustrated in FIG. 9 or orthogonal deflectors 230, 240 in FIG. 2 and the compensation magnet assembly 1010 illustrated in FIG. 10 can be combined into a single PBS system, which can also include beam stop 275, 975. An example of such a combined system is provided in FIG. 14, which illustrates a pencil beam system 1400. Pencil beam system 1400 includes the same components as pencil beam system 1000 with the addition of orthogonal deflector(s) 1430, detector apparatus 1450, optional beam stop 975. Orthogonal deflector(s) 1430 can be the same as or substantially the same as orthogonal deflector(s) 930 or first and second orthogonal deflectors 230, 240, discussed above. Detector apparatus 1450 can be the same as or substantially the same as detector apparatus 950 or first and second detector apparatus 250, 260, discussed above.

In operation, the trajectory correction system including orthogonal deflectors 1430 can be used to adjust/correct the incoming beam 901 trajectory such that it is as ideal as possible for a given beam energy, as discussed above with respect to orthogonal deflector(s) 930 and first and second orthogonal deflectors 230, 240. After the incoming beam 901 trajectory is adjusted/corrected as ideally as possible or practical, the electromagnet settings of the orthogonal deflectors 1430 are then set to the values that provide this adjusted/corrected trajectory. Next, the PBS 1400 can be used to therapeutically treat the patient. During therapeutic treatment of the patient, the compensation magnet assembly 1010 can be used as discussed above (e.g., to make real-time corrections of small position errors, speeding settling at new spot positions, beam blurring/spreading, and/or hysteresis correction). Should the trajectory correction system detect an out-of-tolerance trajectory, then therapy can be temporarily stopped while the electromagnet settings of the orthogonal deflectors 1430 are re-adjusted, and then therapy can resume. In some embodiments, if the controller 970 determines that the compensation magnet assembly 1010 needs to correct the beam trajectory over a predetermined deflection angle limit or threshold or it needs to correct the beam position at isocenter 905 by greater than a predetermined distance, controller 970 can temporarily stop therapy to check and/or correct the incoming beam trajectory with the trajectory correction system.

Those skilled in the art can appreciate from reviewing the present disclosure that the present system and method for using the system would allow for compensation for small mispositioning of the proton beam (regardless of the cause of the mispositioning) where such compensation is by way of feedback based on positional errors. This feedback and compensation using the modest compensation magnet assembly can be achieved accurately and at relatively great speeds compared to coarser means of correction. While the present compensation mechanism is deliberately weak so as to have a limited beam bending power, it is effective in conjunction with the overall system as described above. In an example, the apparatus is used in proton beams having energies in a range of e.g., 70 to 230 MeV. Low-energy beams of about 70 MeV often have larger beam spot sizes than high-energy beams of about 230 MeV. As discussed above, the beam rigidity (i.e., ease of deflection) changes by a factor of 1.89 over this range, and thus a maximum deflection of, e.g., of 3 mm at isocenter for a 230 MeV beam corresponds to a maximum deflection of 5.67 mm at isocenter for a 70 MeV beam. However, a larger maximum deflection at isocenter can be an appropriate compensation for the generally larger beam spot size of a 70 MeV beam, considering the amount of precision in placing such a low-energy dose is less than that of a high-energy (e.g., 230 MeV) dose.

In powering electromagnetic compensation magnet assembly 1010, a power supply may be employed that operates at a higher bandwidth and faster response rate than the main scan amplifiers. In one embodiment, this bandwidth of the compensation magnet power supply is at least five (5) times greater than that of the scan amplifiers for scan magnet(s) 1020. A relatively small number of turns in the compensation magnet windings, a relatively small air gap volume of the compensation magnet, a low inductance of the compensation magnet, a ferrite, powdered iron, or thin laminated silicon steel return yoke, and/or a power supply with a lower current and/or voltage specification can help reach such an increase in compensation system bandwidth, as discussed above.

Another aspect of the present system and method allows for a greater speed in the correction achievable with such compensation magnet assembly relative to the spot irradiation times.

In another aspect, the present system and method can be used to compensate hysteresis in the PBS scan system to account for misalignment, e.g., due to differences in the magnetic history of the system since calibration.

In yet another aspect, the present system including the compensation magnet assembly can act to deliberately enlarge or spread out the effective size of the beam spot achievable by quickly executing a pattern (random or non-random) in two dimensions orthogonal to the direction of the beam. Enlarging the effective beam spot can be useful in reducing the number of beam target locations needed to be treated in the course of a therapy session of an extended surface or volume. Therefore, the wider effective spot size may optimize or improve the overall treatment map by reducing the apparent number of spots needing to be treated directly.

FIG. 15 is a flow chart 1500 illustrating a method for real-time beam position error correction of a charged particle pencil beam according to one or more embodiments. In step 1501, the beam is generated at a desired offset, beam angle, and energy level. When the beam is first generated, the calibration and control parameters are initialized to zero as no correction control signals have been generated. Alternatively, the controller can generate initial control parameters for the beam based on historical data of control parameters used for the beam at the same energy level.

In step 1502, the detector data output from one or more ionization chambers (e.g., ionization chambers 1030) are read and collected through readout electronics. The readout electronics have sufficient bandwidth and processing speed to collect data at about 1 kHz or more.

In step 1503, the controller characterizes the beam position based on the data output from the ionization chamber(s). The characterization includes calculating the measured centroid position of the beam at one or more ionization chambers that measure the beam's position along the "x" axis and one or more ionization chambers that measure the beam's position along the "y" axis, where the x and y axes are orthogonal to each other and to the direction of travel of the beam (along the "z" axis).

In some embodiments, the controller characterizes the projected position of the beam at isocenter based on the measured position(s) of the beam. For example, the controller can characterize the projected position of the beam based on one measured "x" position and one measured "y" position of the beam based on the assumption that the beam deflects at the known longitudinal center of the scan magnet(s), which are disposed upstream of the ionization chamber(s). In other embodiments, the controller characterizes the projected position of the beam at isocenter based on at least two measured "x" and "y" positions of the beam based on the assumption that the beam passes through these positions in a straight line.

In step 1504, the controller compares the characterized beam with a model beam to determine if any error correction is needed. The model beam has a model position or offset (x (model), y (model)), which can be the model position(s) of the beam at the position(s) of the ionization chamber(s) or the model position of the beam at isocenter. The model offset position can be scaled or adjusted based on the measured or projected position used for comparison. In general, the beam error can be defined by the following equations:

$$\Delta x = x(\text{measured or projected}) - x(\text{model})$$

$$\Delta y = y(\text{measured or projected}) - y(\text{model})$$

In step 1505, the controller generates control signals to independently correct for the above errors in the parameters x and y. The control signal can be generated based on an open-loop or a closed-loop control algorithm (e.g., PI or PID, as discussed above). In an open-loop control algorithm, a control value input for compensation magnet assembly 1010 can be changed as a function of at least the beam error, the beam energy, and the response function of the control value input (i.e., the amount of beam spot movement that will result from a given change in control value input at a given beam energy).

In step 1506, the control signals are sent to a compensation magnet assembly (e.g., compensation magnet assembly 1010). The compensation magnet assembly includes one or more low-inductance electromagnets, configured and arranged to deflect a charged particle (proton) pencil beam in a plurality of dimensions, e.g., in a plane orthogonal to (or substantially orthogonal to) the direction of the beam, such as the x-y plane. The control signals cause the compensation magnet assembly to adjust the x and/or y position of the beam according to the offset error determined in step 1504. In some embodiments, the compensation magnet assembly includes a single combined function magnet, for example to minimize its insertion length or footprint along the beam axis.

In step 1507, the process returns to step 1502 (read detector data) to characterize and adjust (if needed) the now-adjusted beam. Thus, the beam can be controlled in a closed loop and corrected iteratively and in real time. The feedback loop illustrated in FIG. 15 has a faster response rate than the feedback loop for the scan magnet, thereby providing a faster method to correct the beam position than previously available.

In some embodiments, the beam adjustment parameters from each scan are stored in a memory. When the beam starts (step 1501), when the energy of the beam changes, and/or when the position of the beam changes, the controller can use historical adjustment parameters (in the same scan run and/or over many scan runs over days, weeks, etc.) at the same energy level and/or position as the starting point for correcting the offset error of the beam. The historical adjustment parameters can provide a relatively good approximation for the necessary adjustment.

FIG. 16 is a flow chart 1600 illustrating a method for spreading a position of a charged particle pencil beam according to an embodiment. Steps 1601-1603 can be the same as or substantially the same as steps 1501-1503, respectively. After the beam position is characterized in step 1603, the controller determines the appropriate beam spread area for the measured beam position. Factors that the controller can use in this determination include the treatment plan, the potential beam spread surrounding the target location, and the dose already delivered to the patient at the target location and at the potential spread region surrounding the target location.

Relevant information from the treatment plan includes the treatment positions for each beam energy level and the desired therapeutic dosage of beam energy to deliver to the patient at each such treatment position. The potential beam spread region can be based on the configuration of the compensation magnet assembly. For example, the compensation magnet assembly can deflect the beam from about 1 mm to about 10 mm in some embodiments, or any value or range therebetween. The effective beam spot position of a spread beam can be a function of the beam spot dimensions and the beam spread amount. The controller can determine the dose already delivered to the patient based on the prior measured positions (and/or effective beam spot position(s)) of the beam, the beam current density at each position, and the length of time that the beam is located at each position.

If positions within the potential beam spread region, including the target position, have already received a partial therapeutic dose, the controller can limit the spread of the beam so that those positions receive only enough beam energy to achieve the target therapeutic dose (e.g., by limiting the time that the beam is located at those positions). If positions within the potential beam spread region, including the target position, have already received a full therapeutic dose, the controller can cause the compensation magnet assembly to avoid those positions.

In step 1605, the controller generates control signals to cause the compensation magnet assembly to spread the beam over the desired beam spread area as determined in step 1604. The control signals can cause the compensation magnet assembly to cover the desired beam spread area by deflecting the beam in a random or a non-random manner or pattern within the desired beam spread area.

In step 1606, the control signals are sent to the compensation magnet assembly (e.g., compensation magnet assembly 1010) to deflect the beam according to the control signals.

In step 1607, the process returns to step 1602 (read detector data) to determine whether the beam position has changed since the last iteration. If the beam position has changed, the controller will determine the desired beam spread area for the new position in the same manner as discussed above. Even if the beam position has not changed, the beam spread area may vary in each iteration based on the total dose administered at each position within the potential beam spread area. For example, if one position received the target therapeutic dose in the last iteration, the controller would not spread the beam to that position in the next (and subsequent) iteration.

Therefore, as described above, those skilled in the art will appreciate that the present disclosure provides a de-coupling of the scanning and the compensation or correction magnets within the controllable limits of each. This de-coupling permits faster correction responses by the compensation magnet assembly, preferably disposed upstream (before) the main magnet assemblies. Overcorrection is avoided on account of the weaker compensation magnet strength so that this does not pose a substantial risk of accidental treatments far from the intended beam target position. An additional benefit of this design as mentioned is the ability to achieve rapid controlled compensation inputs to the PBS system.

The present disclosure should not be considered limited to the particular embodiments described above, but rather should be understood to cover all aspects of the disclosure as fairly set out in the present disclosure. Various modifications, equivalent processes, as well as numerous structures to which the present disclosure may be applicable, will be readily apparent to those skilled in the art to which the present disclosure is directed upon review of the present disclosure.

What is claimed is:

1. A system for providing real-time correction of a charged particle beam, comprising:
    a particle beam generator to generate a generated particle beam parallel to a reference axis;
    a transport beamline apparatus comprising beamline deflector magnets to generate magnetic fields to deflect said generated particle beam along a defined trajectory towards a scan nozzle;
    said scan nozzle comprising:
        at least one scan electromagnet to direct said generated particle beam to a target position on an isocenter plane;
        a detector apparatus disposed between said at least one scan magnet and said isocenter plane, said detector apparatus configured to output a measured position signal representing a measured position of said deflected particle beam in orthogonal first and second planes, wherein said reference axis is orthogonal to said first and second planes;
    a compensation electromagnet assembly disposed between said transport beamline apparatus and said scan nozzle, said compensation electromagnet assembly configured to (a) receive from a control system an offset control signal and (b) generate magnetic fields based on said offset control signal to correct a beam offset error;
    wherein said control system comprises a processor, said control system configured to:
        receive as an input said measured position signal;
        determine said beam offset error based on said measured position and a target position of said generated particle beam; and
        generate said offset control signal based on said beam offset error, and
    wherein a response rate of a first feedback loop comprising said detector apparatus, said control system, and said compensation electromagnet assembly is faster than a response rate of a second feedback loop comprising said detector apparatus, said control system, and said at least one scan electromagnet.

2. The system of claim 1, wherein an inductance of said compensation electromagnet assembly is lower than an inductance of said at least one scan electromagnet.

3. The system of claim 2, wherein said inductance of said compensation electromagnet assembly is about 150 µH.

4. The system of claim 1, wherein a maximum magnetic field of said compensation electromagnet assembly is lower than a maximum magnetic field of said at least one scan magnet.

5. The system of claim 4, wherein said compensation electromagnet is configured to provide a maximum deflection of said generated particle beam of about 3 mm to about 1 cm at said isocenter plane.

6. The system of claim 1, wherein said compensation electromagnet assembly includes a combined function electromagnet.

7. The system of claim 6, wherein said combined function electromagnet includes a multipole electromagnet.

8. The system of claim 1, wherein said compensation electromagnet assembly includes a first pair of electromagnets to deflect the generated particle beam in said first plane and a second pair of electromagnets to deflect the generated particle beam in said second plane.

9. The system of claim 1, wherein said compensation electromagnet assembly is configured to deflect the generated particle beam at an angle to compensate for said beam offset error.

10. The system of claim 1, wherein said compensation electromagnet assembly is configured to have a maximum magnetic field strength to limit said correction of said beam offset error.

11. The system of claim 1, wherein said detector apparatus includes a first strip detector configured to measure said first measured position in said first plane and a second strip detector configured to measure said first measured position in said second plane.

12. The system of claim 1, wherein said first detector apparatus includes a pixelated detector comprising orthogonal detector elements for measuring said first measured position in said first and second planes.

13. A system for spreading a charged particle beam, comprising:
    a particle beam generator to generate a generated particle beam parallel to a reference axis;
    a transport beamline apparatus comprising beamline deflector magnets to generate magnetic fields to deflect said generated particle beam along a defined trajectory towards a scan nozzle;
    a scan nozzle comprising:
        at least one scan electromagnet to direct said generated particle beam to a target position on an isocenter plane;
        a detector apparatus disposed between said at least one scan magnet and said isocenter plane, said detector apparatus configured to output a measured position signal representing a measured position of said deflected particle beam in orthogonal first and second planes, wherein said reference axis is orthogonal to said first and second planes;
    a compensation electromagnet assembly disposed between said transport beamline apparatus and said scan nozzle, said compensation electromagnet assembly configured to (a) receive from a control system a compensation electromagnet control signal and (b)

generate magnetic fields based on said compensation electromagnet control signal to spread said measured beam position;

wherein said control system comprises a processor, said control system configured to:
receive as a first input said measured position signal;
receive as a second input a maximum beam spread of said compensation electromagnet assembly;
determine a compensation beam spread based on said measured position and said maximum beam spread; and
generate said compensation electromagnet control signal based on said compensation beam spread, and
wherein a response rate of a feedback loop comprising said detector apparatus, said control system, and said compensation electromagnet assembly is faster than a response rate of a second feedback loop comprising said detector apparatus, said control system, and said at least one scan electromagnet.

14. The system of claim 13, wherein said control system is configured to receive as a third input a treatment plan for a subject and a dosage history, the dosage history comprising a beam dosage already delivered to the subject at each position in the isocenter plane.

15. The system of claim 14, wherein said control system is configured to determine said compensation beam spread based on said third input.

16. The system of claim 13, wherein said compensation electromagnet control signal includes a compensation beam spread pattern.

17. The system of claim 13, wherein an inductance of said compensation electromagnet assembly is lower than inductance of said at least one scan electromagnet.

18. The system of claim 17, wherein said inductance of said compensation electromagnet assembly is about 150 µH.

19. The system of claim 13, wherein a maximum magnetic field of said compensation electromagnet assembly is lower than a maximum magnetic field of said at least one scan magnet.

20. The system of claim 19, wherein said compensation electromagnet is configured to provide a maximum deflection of said generated particle beam of about 3 mm to about 1 cm at said isocenter plane.

21. The system of claim 13, wherein said compensation electromagnet assembly is configured to deflect the generated particle beam at a plurality of angles to achieve said compensation beam spread.

22. The system of claim 13, wherein said compensation electromagnet assembly includes a combined function electromagnet.

23. The system of claim 22, wherein said combined function electromagnet includes a multipole electromagnet.

24. The system of claim 13, wherein said compensation electromagnet assembly includes a first pair of electromagnets to deflect the generated particle beam in said first plane and a second pair of electromagnets to deflect the generated particle beam in said plane.

* * * * *